United States Patent [19]

Shroot et al.

[11] Patent Number: 4,740,519
[45] Date of Patent: Apr. 26, 1988

[54] BENZO (B) THIOPHENE CARBOXYLATE DERIVATIVES AND PHARMACEUTICAL COMPOSITIONS

[75] Inventors: Braham Shroot, Antibes; Jacques Eustache, Grasse; Jean-Michel Bernardon, Le Rouret, all of France

[73] Assignee: Centre International de Recherches Dermatologiques C.I.R.D., Valbonne, France

[21] Appl. No.: 839,269

[22] Filed: Mar. 13, 1986

Related U.S. Application Data

[63] Continuation-in-part of Ser. No. 777,728, Sep. 19, 1985, abandoned.

[30] Foreign Application Priority Data

Sep. 19, 1984 [LU] Luxembourg ............................ 85544

[51] Int. Cl.$^4$ ...................... A61K 31/38; C07D 333/54
[52] U.S. Cl. ...................... 514/443; 549/57;
549/469; 544/139; 548/180; 548/224; 548/327;
548/334; 548/509; 548/510; 548/466; 514/725;
514/847; 514/863; 514/861; 514/864; 514/880;
514/885; 514/912; 514/914; 514/938; 514/944;
514/962; 514/969; 514/859; 424/59; 424/60;
424/70; 424/69; 424/47; 424/DIG. 4
[58] Field of Search ............................ 549/57; 514/443

[56] References Cited
U.S. PATENT DOCUMENTS
4,456,618 6/1984 Dawson et al. ........................ 549/57

Primary Examiner—Robert W. Ramsuer
Attorney, Agent, or Firm—Cushman, Darby & Cushman

[57] ABSTRACT

Aromatic heterocyclic derivatives have the formula

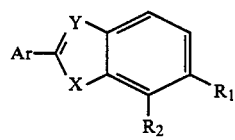

wherein $R_1$ represents

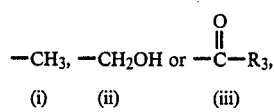

wherein $R_3$ represents hydrogen, $-OR_4$ wherein $R_4$ represents hydrogen, alkyl having 1–20 carbon atoms or mono- or polyhydroxyalkyl or $R_3$ represents

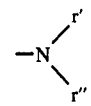

wherein r' and r'' represent hydrogen, lower alkyl or together form a heterocycle, $R_2$ represents hydrogen or $-CH_3$ and Ar represents

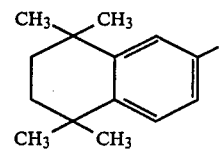 (A)

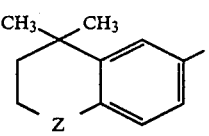

(B)

wherein Z is O or S,

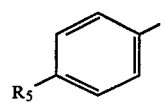 (C)

wherein $R_5$ is lower alkyl or

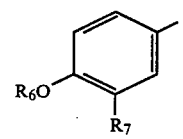 (D)

wherein $R_6$ is hydrogen or alkyl having 1–10 carbon atoms and $R_7$ represents alkyl having 4–12 carbon atoms or cycloalkyl, Y is CH or a nitrogen atom and X represents oxygen, sulfur or $-N-R_8$ when $R_8$ represents hydrogen, lower alkyl or lower alkoxycarbonyl, with the proviso that (i) when Y is CH and X is oxygen or sulfur Ar is other than C and (ii) when Y is nitrogen and X is oxygen, Ar is other than (C) or (D) in which $R_6$ is alkyl having 1–4 carbon atoms and $R_7$ is branched alkyl having 4–12 atoms useful in veterinary or human therapy and in cosmetic formulations.

6 Claims, No Drawings

BENZO (B) THIOPHENE CARBOXYLATE DERIVATIVES AND PHARMACEUTICAL COMPOSITIONS

This application is a continuation-in-part of our application Ser. No. 777,728, filed Sept. 19, 1985 now abandoned.

The present invention relates to new aromatic heterocyclic derivatives, to a process for their preparation and to their use in veterinary or human therapy and in cosmetic formulations.

These new heterocyclic dervatives exhibit a biologic profile which permits them to be classified with compounds known as "retinoides", the most common of which are the cis and trans retinoic acids (tretinoine and isotretinoine;) and etretinate.

Compared to known retinoides, the aromatic heterocyclic compounds of the present invention, due to their structure, exhibit better stability to light and oxygen. Moreover, they exhibit improved activity in the systemic and topical treatment of dermatologic ailments linked to a keratinization disorder (differentiation proliferation) and dermatologic aliments, or others, with inflammatory and/or immuno-allergic components, as well as an anti-tumoral activity. Besides, these products can be employed in the treatment of atrophy, be it cutaneous or respiratory.

These compounds are also usefully employed in the field of ophthamology and principally in the treatment of corneopathy.

The aromatic heterocyclic compounds of the present invention, also hereinunder defined under the denomination of "Hetero-Differins" due to their chemical structure and activity, can be represented by the following formula:

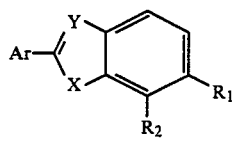

(I)

wherein

R$_1$ represents

—CH$_3$, —CH$_2$OH or —C(=O)—R$_3$,
(i)       (ii)            (iii)

wherein R$_3$ represents hydrogen, —OR$_4$ wherein R$_4$ represents hydrogen, alkyl having 1-20 carbon atoms, mono or polyhydroxyalkyl, or R$_3$ represents

wherein r' and r" each independently represent hydrogen or lower alkyl or r' and r" together with the nitrogen atom to which they are attached form a heterocycle, R$_2$ represents hydrogen or —CH$_3$, Ar represents an aromatic radical having one of the following formulas:

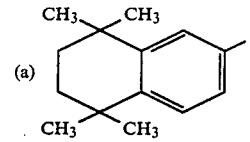

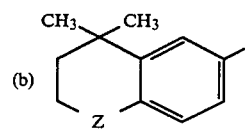

wherein Z is O or S;

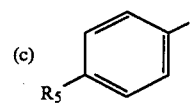

wherein R$_5$ is lower alkyl; and

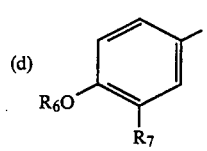

wherein

R$_6$ is hydrogen or alkyl having 1–10 carbon atoms and R$_7$ is branched alkyl having 4–12 carbon atoms or cycloalkyl;

Y represents CH or a nitrogen atom, and

X represents oxygen, sulfur or —NR$_8$, wherein R$_8$ represents hydrogen, lower alkyl or lower alkoxy carbonyl, with the provisos that: (i) when Y represents CH and Y represents oxygen or sulfur, Ar is other than the radical of formula (C) wherein R$_5$ is —CH$_3$ and (ii) when Y represents nitrogen and X represents oxygen, Ar is other than the radical of formula (C) or of formula (D) wherein R$_6$ represents alkyl having 1–4 carbon atoms and R$_7$ represents branched alkyl having 4–12 carbon atoms.

By lower alkyl is meant an alkyl radical having from 1–6 carbon atoms and principally methyl, ethyl, isopropyl, butyl and t-butyl.

By monohydroxyalkyl is meant a radical having 2 or 3 carbon atoms, and principally 2-hydroxyethyl and 2-hydroxypropyl.

By polyhydroxyalkyl is meant a radical derived from glycerol, pentaerythritol or mannitol.

By lower alkoxycarbonyl is meant a radical having an alkoxy chain, branched or not, having 1–14 carbon atoms. Representative preferred lower alkoxycarbonyl radicals include methoxy carbonyl, ethoxy carbonyl, isopropoxy carbonyl and t-butoxy carbonyl.

When r' and r" taken together form a heterocycle, the heterocycle can be piperidino, piperazino, morpholino or pyrrolidino.

When R$_7$ represents cycloalkyl, the cycloalkyl radical is, preferably, cyclohexyl, 1-methyl cyclohexyl or adamantyl.

In accordance with one particular embodiment of the present invention, the aromatic heterocyclic compound has the following formula:

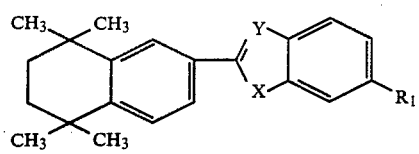

wherein
R₁ represents —CH₂OH or

wherein R₃ represents —O—R₄ or

wherein R₄ represents hydrogen, —CH₃ or —CH₂CH₂OH and r' and r" each independently represent hydrogen, or lower alkyl, or r' and r" taken together with the nitrogen atom to which they are attached form a morpholino ring,
Y represents CH or a nitrogen atom, and
X represents sulfur, oxygen or N—R₈ wherein R₈ represents hydrogen, —CH₃ or —CO₂ t-butyl;

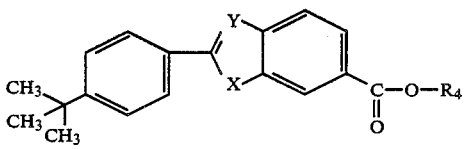

wherein
R₄ represents hydrogen or —CH₃,
Y represents CH or a nitrogen atom, and
X represents sulfur, oxygen or N—R₈ wherein R₈ represents hydrogen or —CO₂ t-butyl; and

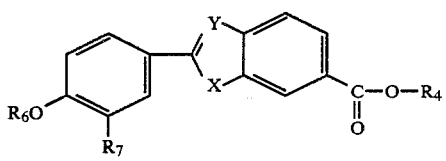

wherein
R₄ represents hydrogen or —CH₃,
R₆ represents —CH₃ or —C₁₀H₂₁,
R₇ represents t-butyl, 1,1-dimethyldecyl or adamantyl,
Y represents CH or a nitrogen atom, and
X represents sulfur, oxygen or N—R₈ wherein R₈ represents hydrogen.

Representative preferred "Hetero-Differins" of formula I include:
methyl 2-(p-t-butylphenyl)-6-benzo(b)thiophene carboxylate,
2-(p-t-butylphenyl)-6-benzo(b)thiophene carboxylic acid,
methyl 2-(5,6,7,8-tetrahydro-5,5-8,8-tetramethyl-2-naphthyl)-6-benzo(b)thiophene carboxylate,
2-(5,6,7,8-tetrahydro-5,5,8,8,-tetramethyl-2-naphthyl)-6-benzo(b)thiophene carboxylic acid,
methyl 2-(p-t-butylphenyl)-benzo(b)furan carboxylate,
2-(p-t-butylphenyl)-benzo(b)furan carboxylic acid,
methyl 2-(5,6,7,8-tetrahydro-5,5,8,8-tetramethyl-2-naphthyl)-6-benzo(b)furan carboxylate,
2-(5,6,7,8-tetrahydro-5,5,8,8-tetramethyl-2-naphthyl)-6-benzo(b)furan carboxylic acid,
methyl 1-t-butoxycarbonyl-2-(p-t-butylphenyl)-6-indolecarboxylate,
2-(p-t-butylphenyl)-6-indolecarboxylic acid,
methyl 1-t-butoxycarbonyl-2-(5,6,7,8-tetrahydro-5,5,8,8,-tetramethyl-2-naphthyl)-6-indolecarboxylate,
methyl 2-(5,6,7,8-tetrahydro-5,5,8,8-tetramethyl-2-naphthyl)-6-indolecarboxylate,
2-(5,6,7,8-tetrahydro-5,5,8,8-tetramethyl-2-naphthyl)-6-indolecarboxylic acid,
methyl 1-methyl-2-(5,6,7,8-tetrahydro-5,5,8,8-tetramethyl-2-naphthyl)-6-indolecarboxylate,
1-methyl-2-(5,6,7,8-tetrahydro-5,5,8,8-tetramethyl-2-naphthyl)-6-indolecarboxylic acid,
methyl 2-(p-t-butylphenyl)-5-benzimidazole carboxylate,
2-(p-t-butylphenyl)-5-benzimidazole carboxylic acid,
methyl 2-(5,6,7,8-tetrahydro-5,5,8,8-tetramethyl 2-naphthyl)-benzimidazole carboxylate,
2-(5,6,7,8-tetrahydro-5,5,8,8-tetramethyl-2-naphthyl)-benzimidazole carboxylic acid,
methyl 2-(5,6,7,8-tetrahydro-5,5,8,8-tetra methyl-2-naphthyl)-6-benzoxazole carboxylate,
2-(5,6,7,8-tetrahydro-5,5,8,8-tetramethyl-2-naphthyl)-6-benzoxazole carboxylic acid,
the morpholide of 2-(5,6,7,8-tetrahydro-5,5,8,8-tetramethyl-2-naphthyl)-6-benzoxazole carboxylic acid,
the ethylamide of 2-(5,6,7,8-tetrahydro-5,5,8,8-tetramethyl-2-naphthyl)-6-benzoxazole carboxylic acid,
the 2-hydroxyethyl ester of 2-(5,6,7,8-tetrahydro-5,5,8,8-tetramethyl-2-naphthyl)-6-benzoxazole carboxylic acid,
2-(5,6,7,8-tetrahydro-5,5,8,8-tetramethyl-2-naphthyl)-6-benzoxazolyl methyl alcohol,
the methyl ester of 2-[3-(1-adamantyl)-4-methoxyphenyl]-5-benzimidazole carboxylic acid,
the methyl ester of 2-[3-(1-adamantyl)-4-methoxyphenyl]-6-benzoxazole carboxylic acid,
2-[3-(1-adamantyl)-4-methoxyphenyl]-6-benzoxazole carboxylic acid,
the methyl ester of 2-[3-(1-adamantyl)-4-decyloxyphenyl]-6-benzoxazole carboxylic acid,
2-[3-(1-adamantyl)-4-decyloxyphenyl]-6-benzoxazole carboxylic acid,
the methy ester of 2-[3-(1-adamantyl)-4-methoxyphenyl]-6-benzo(b)furan carboxylic acid,
2-[3-(1-adamantyl)-4-methoxy phenyl]-6-benzo(b)furan carboxylic acid,
the methyl ester of 2-[3-(1-adamantyl)-4-methoxyphenyl]-6-benzo(b)thiophene carboxylic acid,
2-[3-(1-adamantyl)-4-methoxyphenyl]-6-benzo(b)thiophene carboxylic acid,
the methyl ester of 2-(3-t-butyl-4-methoxyphenyl)-6-benzo(b)furan carboxylic acid,
2-(3-t-butyl-4-methoxyphenyl)-6-benzo(b)furan carboxylic acid,
the methyl ester of 2-[3-(1,1-dimethyldecyl)-4-methoxyphenyl]-6-benzo(b)furan carboxylic acid,
2-[3-(1,1-dimethyldecyl)-4-methoxyphenyl]-6-benzo(b)furan carboxylic acid, 2-[3-(1-adamantyl)-4-methoxyphenyl]-5-benzimidazole carboxylic acid, the methyl ester of 2-[3-(1-adamantyl-4-hydroxyphenyl]-5-benzimidazole carboxylic acid, the methyl ester of 2-(5,6,7,8-tetrahydro-5,5,8,8-tetramethyl-2-naphthyl)-6-benzo thiazole carboxylic acid, 2-(5,6,7,8-tetrahydro-5,5,8,8-tetramethy-2-naphthyl)-6-benzothiazole carboxylic acid, and the methyl ester of 2-(4,4-dimethyl-2,3-dihydro-1-benzopyran-6-yl)-5-benzimidazole carboxylic acid.

Various synthesis methods can be employed in the production of the compounds of formula (I). Representative methods include, in particular, the following processes:

(a) First method (Scheme I)

This method comprises reacting a derivative of an aromatic carboxylic acid of formula (1) with an ester of an aromatic carboxylic acid of formula (2) having an amino radical in the 4-position and an amino, hydroxy or thio radical in the 3-position.

This method is quite particularly preferred when, in the compounds of formula I, the radical Y is represented by a nitrogen atom.

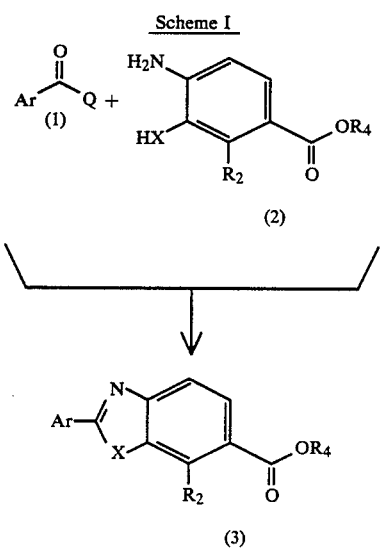

Q = OH or Cl
X = NH, O or S (B) Second Method (Scheme II)

This method comprises reacting a derivative of an aromatic carboxylic acid of formula (1) with an ester of an aromatic carboxylic acid of formula (4) having in the 4-position a methyl radical and an amino, hydroxy or thio radical in the 3-position.

The resulting intermediate compound (5) is then brominated so as to yield a bromo derivative methylated in the 4-position, (6). After reaction with a triaryl or trialkyl phosphine, or with a triaryl or trialkyl phosphite, or even with an arylphosphine oxide, a compound (7) is obtained which is then cyclized into the compound of formula (8).

This method is quite particularly preferred when, in the compounds of formula (I), Y represents CH.

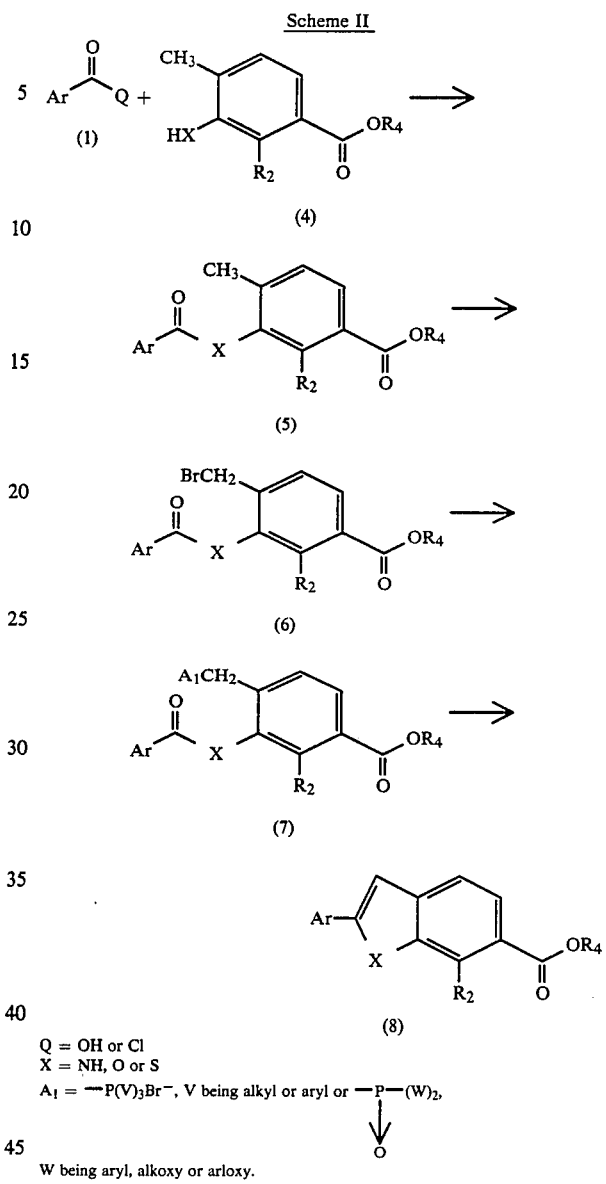

Q = OH or Cl
X = NH, O or S
$A_1 = -P(V)_3Br^-$, V being alkyl or aryl or $-P-(W)_2$,
$\downarrow$
$O$ W being aryl, alkoxy or arloxy.

In accordance with this latter method, the cyclization reaction, i.e., the conversion of compound (7) into compound (8) is carried out in the presence of a base which can be a hydroxide or a carbonate of an alkali metal, for example, lithium hydroxide or potassium carbonate, a hydride of an alkali metal for example, sodium hydride, an alcoholate of an alkali metal for example sodium methylate or potassium t-butoxide, a tertiary amine for example triethylamine, diisopropylethylamine or diazabicycloundecene (DBU) or even an alkali amide for example, sodium amide or lithium di-isopropyl amide. The temperature of the reaction is between −10° C. and +150° C. and there can be employed, as a solvent, a dipolar aprotic solvent (dimethyl sulfoxide or dimethyl formamide), an alcohol, an ether (dioxan or tetrahydrofuran). The reaction is advantageously carried out in tetrahydrofuran (THF) at a temperature between 0° C. and 80° C. while using triethylamine or DBU as the base.

The bromination reaction, i.e., the production of compounds of formula (6) is carried out in the presence of N-bromosuccinimide in previously dried benzene or carbon tetrachloride, the temperature preferably being between 70° C. and 90° C. and with a free radical initiator preferably being benzoyl peroxide.

The acylation reaction followed by a dehydrating cyclization reaction according to Scheme I, as well as the acylation reaction according to Scheme II, is carried out in a known manner. When X represents NH, the reaction is advantageously effected by using a compound of formula (1) in the form of an acid chloride (Q=Cl) in the presence of a tertiary amine.

The dehydrating cyclization reaction, according to Scheme I, is preferably carried out by means of an acid catalyst, for example, p-toluene sulfonic acid at the reflux of the solvent, preferably xylene.

The esters obtained in accordance with the methods described above can be converted, according to known procedures, into various analogs which are the objects of meanings (i) to (iii) for the radical $R_1$.

Thus, the saponification of these esters gives corresponding acids. These acids can be transformed into acid chlorides which are then easily converted into amides. These amides can also be obtained by the direct action of amines on the esters obtained earlier. The reduction of the esters, aldehydes or amides by an appropriate reducing agent (for example, lithium aluminohydride) permits access to corresponding alcohols and amines.

When the compounds according to the present invention are provided in the form of salts, the salts can be those of an alkali or alkaline earth metal or organic amines. When the compounds of formula I are provided in the form of a free acid, or they can be salts of mineral or organic acids when the compounds of formula I are provided in the form of a free amine.

The present invention also relates to a new intermediate compound having the formula $$\underset{R_3O}{\underset{|}{\bigodot}}\!\!-R_1 \quad (V)$$

wherein
  $R_1$ represents a halogen selected from the group consisting of Cl, Br and I, or —COOH,
  $R_2$ represents $\alpha,\alpha'$ disubstituted alkyl having 4 to 12 carbon atoms, or cycloalkyl having 5-10 carbon atoms, the carbon atom in the $\alpha$ position being tertiary, and
  $R_3$ represents hydrogen, linear or branched alkyl having 1-10 carbon atoms or $$Si \begin{array}{c} R_4 \\ -R_5 \\ R_4 \end{array}$$

wherein $R_4$ represents lower alkyl having 1-4 carbon atoms and $R_5$ represents lower alkyl having 1-4 carbon atoms or phenyl.

The expression, "$\alpha,\alpha'$ disubstituted alkyl having 4 to 12 carbon atoms", means tert. butyl, 1,1-dimethylpropyl, 1-methyl-2-ethyl propyl, 1-methyl-2-ethyl hexyl or 1,1-dimethyl decyl.

The expression, "cycloalkyl having 5-10 carbon atoms, the carbon atom in the $\alpha$ position being tertiary" means 1-methyl cyclohexyl or 1-adamantyl.

Representative intermediate compounds of Formula V include:
(1) 2-(1-adamantyl)-4-bromophenol,
(2) 2-(1-adamantyl)4-bromodecyloxy benzene,
(3) 3-(1-adamantyl)-4-decyloxy benzoic acid,
(4) 2-(1-adamantyl)-4-bromo-tert.butyldimethyl siloxy benzene,
(5) 3-(1-adamantyl)-4-tert.-butyldimethyl siloxy benzoic acid,
(6) 3-(1-adamantyl)-4-methoxy benzoic acid,
(7) 2-(1-adamantyl)-4-bromo anisole,
(8) 4-bromo-2-(1,1-dimethyldecyl)-phenol,
(9) 4-bromo-2-(1,1-dimethyldecyl)-anisole,
(10) 3-(1,1-dimethyldecyl)-4-methoxy-benzoic acid,
(11) 4-bromo-3-tert.-butyl methoxy benzene and
(12) 3-tert.-butyl-4-methoxybenzoic acid.

The present invention also relates to a process for preparing the intermediate compounds of Formula V according to the following reaction scheme:

$$\underset{HO}{\bigodot}\!\!-X \longrightarrow \underset{HO}{\overset{R_2}{\bigodot}}\!\!-X \longrightarrow$$

(9)     (10)

$$\underset{R_3O}{\overset{R_2}{\bigodot}}\!\!-X \longrightarrow \underset{R_3O}{\overset{R_2}{\bigodot}}\!\!-COOH ,$$

(11)     (12)

wherein X=halogen.

This process comprises reacting a p-halogenophenol (9) with an alkyl halide or an alkene or even a cycloalkanol in the presence of aluminum trichloride or in the case of a cycloalkanol in the presence of sufuric acid, in an organic solvent such as dichloromethane or nitrobenzene. The substituted p-halogenophenol (10) obtained is then O-alkylated using an alkyl halide or a trialkyl halide or dialkylphenyl-silyl in accordane with conventional procedures, that is, preferably by the formation of sodium phenate.

Starting with compound (11) the corresponding benzoic acid is produced by the reaction of $CO_2$ on the magnesium derivative of (11).

The compounds according to the present invention have good to excellent activity in the inhibition test of ornithine decarboxylase in nude rats after induction by "tape stripping". This test is considered a measure of the action of the retinoides on the phenomena of cellular proliferation.

These compounds are particularly appropriate for treating dermatologic ailments linked to a keratinization disorder (differenciation, proliferation) as well as dermatologic disease, or others, having an inflammatory and/or immunoallergic component or cutaneous or respiratory atrophy, principally:
  acne vulgaris, blackheads or polymorphs, solar senile acne, and medicinal or professional acne, extensive and/or severe forms of psoriasis, and other keratinization disorders, and principally ichtyoses and ichtysosis-like conditions, Darier malady, palmo-plantar keratodermies, leucoplasies and leuco-plasie like states, lichen plan, all malignant or benign dermatologic proliferations, severe or extensive, eczema and asthma.

The compounds of the present invention are also active in the treatment of certain rheumatoid disorders, principally psoriasic rheumatism. They are also useful in the treatment of certain ophthalmologic problems related to the cornea.

The present invention also relates to a medicine comprising at least one compound of formula I and/or one of its salts as defined above.

The present invention further relates to a new medicinal composition, intended principally for the treatment of the disorders mentioned above, said composition comprising, in a pharmaceutically acceptable vehicle, at least one compound of formula I.

As has been indicated above, the "Hetero-Differins" according to the present invention exhibit, relative to known retinoides, better stability to light and oxygen, this advantage being essentially due to the fact that they do not possess easily isomerized double bonds.

The compounds according to the present invention are generally administered at a daily dosage of about 2 µg/kg to 2 mg/kg or body weight.

As the vehicle or support for these compositions, any conventional support can be employed, the active compound being found in the dissolved state or in the dispersed state in the said support.

The administration of the compounds of the present invention can be carried out enterally, parenterally, topically or ocularly. When administered enterally, the medicines can be provided in the form of tablets, gelules, pills, syrups, suspensions, solutions, powders, granules or emulsions.

When administered parenterally, the medicinal compositions can be provided in the form of solutions or suspensions for perfusion or injection.

When administered topically, the pharmaceutical compositions, based on the compounds of the present invention, can be provided in the form of ointments, tinctures, creams, pommades, powders, pads, impregnated tampons, solutions, lotions, gels, sprays or suspensions. The topically applied compositions contain, preferably, from 0.0005 to about 5% by weight of the compound(s) of formula I based on the total weight of the composition.

These topically applied compositions can be provided either under an anhydrous form or an aqueous form according to clinical indications.

When administered ocularly, the medicinal composition is provided principally in the form of a collyrium or eye-wash.

The compounds of formula I, according to the present invention are also useful in the field of cosmetics, in particular in capillary and body hygiene compositions and principally for acne, for the growth of hair, to combat hair loss, to combat against an oily appearance of the skin or hair or in the treatment of harmful effects of the sun, or even to combat against physiologically dry skin.

The present invention thus relates to a cosmetic composition containing, in a cosmetically acceptable vehicle, at least one compound of formula I, this composition being provided principally in the form of a lotion, gel, soap, shampoo or cream.

The concentration of the compound(s) of formula I, in these cosmetic compositions is between 0.0005 and 2% by weight, preferably between 0.01 and 1% by weight, based on total weight of the composition.

The medicinal and cosmetic compositions according to the invention can contain inert additives or even pharmacodynamically or cosmetically active adjuvants and principally: hydrating agents such as thiamorpholinone and its derivatives or urea, antiseborrheic agents such as S-carboxymethyl cysteine, S-benzyl-cysteamine and their derivatives, tioxolone, anti-acne agents, antibiotics such as erythromycin and its esters, neomycin, tetracyclines, 4,5-polymethylene-3-isothiasolinones, agents favoring hair growth such as "Minoxidil" (2,4-diamino-6-piperidino-3-pyrimidine oxide) and its derivatives; anthralin and its derivatives; Diazoxide (3-chloromethyl-1,2,4-benzothiadiazine-1,1-dioxide), Phenytoin (5,5-diphenyl-2,4-imidazolidinedione) and oxapropanium iodide; steroidic and non-steroidic anti-inflammatory agents; carotenoides and, principally, β-carotene; anti-psoriasic agents, such as anthralin and its derivatives, 5,8,11,14-eicosatetraynoic and 5,8,11 eicosatriynoic acids, their esters and amides.

The compositions according to the present invention can also contain flavor improving agents, preservatives, stabilizers, humidity regulatory agents, pH regulating agents, osmotic pressure modifying agents, emulsifying agents, UV-A and UV-B filter, antioxidants such as α-tocopherol, butylhydroxyanisole or butylhydroxy toluene.

The following non-limiting examples illustrate the preparation of the active compounds of formula I according to the invention as well as compositions containing these compounds.

EXAMPLE 1 methyl 2-(p-t-butylphenyl)-6-benzo(b)thiophenecarboxylate (a) methyl 3-(p-t-butylbenzoylthio)-4-methyl benzoate.

In 20 ml of dry THF there are successively added 1.80 g (10 mmol) of methyl 3-mercapto-4-methyl benzoate, 1.11 g (1.5 ml, 11 mmole) of triethylamine and 2.20 g (11 mmol) of p-t-butyl benzoyl chloride. This mixture is stirred for 2 hours at 20° C., poured into water (100 ml) and subsequently extracted with dichloromethane (3×100 ml). The organic phase is dried; the solvents are evaporated; and the remainder purified by passage through a short silica column (5×10 cm) by eluting with a mixture of dichloromethane (50%) and hexane (50%). The product exhibiting a Rf=0.35 (eluant: dichloromethane) is recovered and on evaporation of the solvents, methyl 3-(p-t-butylbenzoylthio)-4-methyl benzoate (3.0 g, -90%) is obtained.

(b) Methyl 4-bromomethyl-3-(p-t-butylbenzoylthio)-benzoate 2.80 g of the ester obtained in part (a) above, are dissolved in 20 ml of dry carbon tetrachloride, at reflux. 20 mg of benzoyl peroxide are added and, in portions, 1.45 g (8.15 mmol) of N-bromosuccinimide. The mixture is heated at reflux for 10 hours at which point 0.145 g (0.8 mmol of N-bromo succinimide is added. This mixture is then heated for 4 hours at reflux. The solvents are evaporated and the residue is imperfectly purified by passage through a short silica column (5×10 cm) by eluting with dichloromethane. A mixture of 3 products exhibiting the following Rfs: 0.35, 0.40 and 0.45, (eluant: dichloromethane) is obtained. These products are, in order of decreasing polarity: the starting product, the monobrominated product and the dibrominated product. This latter product is removed by chromotography ("Waters" Prep 500, silica column, eluant: mixture of dichloromethane 50%, and hexane, 50%).

There are thus obtained 3.20 g of an oil containing about 80% of the desired ester and about 20% of the starting product.

(c) methyl 2-(p-t-butylphenyl)-6-benzo(b)thiophene carboxylate.

In 20 ml of THF, there are dissolved 3.10 of the mixture obtained in part (b) above, and 1.85 g (7 mmol) of triphenylphosphine. This mixture is heated at reflux under a nitrogen atmosphere for 4 hours. Thereafter, the reaction mixture is cooled and 1.06 g (7 mmol) of diazabicycloundecene (DBU) are added thereto in a dropwise fashion. During the addition of each drop a transitory appearance of a deep yellow color is observed. At the end of the addition, a light precipitate is observed. The reaction mixture is then heated to 50° C. for 15 minutes at which point it is poured into water (100 ml), extracted with dichloromethane (3×100 ml) and dried. The solvents are evaporated and the desired product is obtained by chromatography (silica column, eluant: mixture of dichloromethane, 20%, and hexane, 80%). The resulting solid is recrystallized in hexane, yielding methyl 2-(-p-t-butylphenyl)-6-benzo(b)thiophene carboxylate (1.60 g, 62% starting from the ester obtained in part 1a).

Melting point=155° C.; Rf=0.70 (eluant: mixture of dichloromethane, 20% and hexane, 80%).

EXAMPLE 2

2-(p-t-butylphenyl)-6-benzo(b)thiophenecarboxylic acid 1.2 g (3.7 mmol) of the ester obtained in Example 1(c) are suspended in 100 ml of a 2N soda solution in methanol. The suspension is heated for 4 hours at reflux, then poured into water (100 ml), acidified to pH 0 with concentrated HCl, extracted with ethyl ether (3×100 ml), dried and the solvents evaporated. The resulting solid is recrystallized in acetonitrile, yielding 2-(p-t-butylphenyl)-6-benzo(b)thiophene carboxylic acid. (1.05 g; 91%).

Melting point: 318° C. Rf=0.7 (eluant: mixture of dichloromethane, 80% and methanol, 20%).

EXAMPLE 3 methyl 2-(5,6,7,8-tetrahydro-5,5,8,8-tetramethyl-2-naphthyl)-6-benzo(b)thiophene carboxylate.

(a) methyl 4-methyl-3-(5,6,7,8-tetrahydro-5,5,8,8-tetramethyl-2-naphtoylthio)benzoate.

In a manner analogous to Example 1(a), starting with 1.83 g (10 mmol) of methyl 3-mercapto-4-methyl benzoate, 1.5 ml of triethylamine and 2.76 g (11 mmol) of 5,6,7,8-tetrahydro-5,5,8,8-tetramethyl-2-naphtoyl chloride, methyl 4-methyl-3-(5,6,7,8-tetrahydro-5,5,8,8-tetramethyl-2-naphtoylthio)benzoate (3.50 g; 88%) is produced.

Melting point: 120° C. Rf=0.7 (by using dichloromethane as the eluant).

(b) methyl 4-bromomethyl-3-(5,6,7,8-tetrahydro-(5,5,8,8-tetramethyl-2-naphtoylthio)benzoate.

In a manner analogous to Example 1(b), starting with 3.30 g (8.3 mmol) of the ester obtained in Example 3(a), above, 1.48 g (8.3 mmol) of N-bromosucciminide, and 20 mg of benzoyl peroxide, there is obtained, after chromotography ("Waters" Prep 500, silica column, eluant: a mixture of dichloromethane, 60% and hexane, 40%), a mixture containing about 10% of the starting product and about 90% of methyl 4-bromomethyl-3-(5,6,7,8-tetrahydro-5,5,8,8-tetramethyl-2-naphtoylthio)-benzoate. (2.50 g).

(c) methyl 2-(5,6,7,8-tetrahydro-5,5,8,8-tetramethyl-2-naphothyl)-6-benzo(b)thiophenecarboxylate.

In a manner analogous to Example 1(c), starting with 2.40 g of the mixture obtained in Example 3(b) and 1.6 g of triphenylphosphine, in 15 ml of THF, there is obtained after reflux for 6 hours, a phosphonium salt which is immediately treated with 0.9 ml of DBU. After treatment in a manner analogous to Example 1(c) and after chromatography (silica column, eluant: mixture of dichloromethane, 30% and heptane, 70%) methyl 2-(5,6,7,8-tetrahydro-5,5,8,8-tetramethyl-2-naphthyl)-6-benzo(b)thiophene carboxylate is obtained (1.50 g, 50% based on the starting ester obtained in part 3a, above).

Melting point: 170° C., Rf=0.8 (eluant: dichloromethane).

EXAMPLE 4

2-(5,6,7,8-tetrahydro-5,5,8,8-tetramethyl-2-naphthyl)-6-benzo(b)thiophene carboxylic acid.

In a manner analogous to Example 2, starting with 1.10 g (2.9 mmol) of the ester produced in Example 3(c), 2-(5,6,7,8-tetrahydro-5,5,8,8-tetramethyl-2-naphthyl)-6-benzo(b)thiophene carboxylic acid is produced (0.99 g, 93%).

Melting point: 297° C., Rf=0.7 (eluant: mixture of dichloromethane, 80% and methanol, 20%).

EXAMPLE 5 methyl 2-(p-t-butylphenyl)-6-benzo(b) furan carboxylate (a) methyl 3-(p-t-butylbenzoyloxy)-4-methyl benzoate.

In a manner analogous to Example 1(a) starting with 3.30 g (20 mmol) of methyl 3-hydroxy-4-methyl benzoate, triethylamine (2.20 g, 22 mmol) and p-t-butylbenzoyl chloride (3.90 g, 20 mmol) in 40 ml of THF, methyl 2-(p-t-butylbenzoyloxy)-4-methyl benzoate is obtained (5.30 g, 81%).

Rf=0.45 (eluant: mixture of ethylether, 30% and hexane, 70%.

(b) methyl 4-bromomethyl-3-(p-t-butylbenzoyloxy)-benzoate.

In a manner analogous to Example 1(b), starting with 1.60 g. (5 mmol) of the ester produced in Example 5, part (a), above, 1.30 g of N-bromosuccinimide and benzoyl peroxide (10 mg), dissolved in 5 ml of carbontetrachloride and brought to reflux under a nitrogen atmosphere for 20 minutes, there is produced after chromotography (HPLC, "ZORBAX SIL" column, eluant: mixture of dichloromethane, 80% and hexane, 20%), methyl 4-bromomethyl-3-(p-t-butylbenzoyloxy)benzoate. (0.94 g, 46%).

Melting point: 107° C., Rf=0.40 (eluant: mixture of ethyl ether, 30% and hexane, 70%).

(c) methyl 2-(p-t-butylphenyl)-6-benzo(b)furan carboxylate

In a manner analogous to Example 1(c), starting with 0.52 g (1.30 mmol) of the ester produced in Example 5, part (b), and triphenylphosphine (0.40 g) in 2 ml of THF, the crude desired ester is produced after heating at reflux for 4 hours under a nitrogen atmosphere and then treating with DBU (0.30 g) initially for 15 minutes at 20° C. and for then 15 minutes at reflux. After purification of the crude ester (HPLC, "ZORBAX SIL" column, eluant: mixture of diisopropyl ether, 10% and heptane, 90%), methyl 2-(p-t-butylphenyl)-6-benzo(b)furan carboxylate is obtained (0.35 g, 87%).

Melting point: 148° C., Rf=0.55 (eluant: mixture of ethylether, 30% and heptane, 70%).

EXAMPLE 6

2-(p-t-butylphenyl)-6-bromo(b) furan carboxylic acid 0.30 g (1 mmol) of the ester produced in Example 5(c) is dissolved in 10 ml of ethanol. 2 ml of 5N potash are then added and the mixture is heated for 2 hours at 50° C. The resulting precipitate is dissolved by the addition of water (30 ml) to which is added 10 ml of 1N HCl. The mixture is extracted with 150 ml of ethyl ether, washed with water to a pH of 6 and the solvent evaporated. The resulting residue is dried and dissolved in THF (20 ml). On evaporation of the THF, 2-(p-t-butylphenyl)-6-benzo(b)furan carboxylic acid is obtained. (0.28 g, 98%).

Melting point: 294° C., Rf=0.60 (eluant: mixture of dichloromethane, 80% and methanol, 20%).

EXAMPLE 7

Methyl 2-(5,6,7,8-tetrahydro 5,5,8,8-tetramethyl-2-naphothyl)-6-benzo(b)furan carboxylate (a) Methyl 5'-carboxymethyl-2'-methylphenyl-5,6,7,8-tetrahydro-5,5,8,8-tetramethyl-2-naphthoate.

In a manner analogous to Example 5(a), starting with 3.32 g (20 mmol) of methyl 3-hydroxy-4-methyl benzoate, and 5.51 g (22 mmol) of 5,6,7,8-tetrahydro-5,5,8,8-tetramethyl-2-naphtoyle chloride, methyl 5'-carboxymethyl-2'-methylphenyl-5,6,7,8-tetrahydro-5,5,8,8-tetramethyl-2-naphthoate is obtained 7.10 g, 93%).

Melting point: 159° C., Rf=0.6 (eluant: mixture of ethyl ether, 50% and hexane, 50%).

(b) Methyl 2-bromomethyl-5'-carboxymethyl phenyl-5,6,7,8-tetrahydro-5,5,8,8-tetramethyl-2-naphthoate.

In a manner analogous to Example 5(b), starting with 1.33 g (3.5 mmol) of the ester obtained in Example 7(a), above, methyl 2'-bromomethyl-5-carboxymethyl phenyl-5,6,7,8-tetrahydro-5,5,8,8-tetramethyl-2-naphthoate is obtained (1.00 g, 62%).

Melting point: 119° C., Rf=0.4 (eluant: mixture of ethyl ether, 30% and hexane, 70%).

(c) Methyl 2-(5,6,7,8-tetrahydro-5,5,8,8-tetramethyl-2-naphthyl-6-benzo(b)furan carboxylate.

In a manner analogous to Example 5(c), starting with 0.76 g (1.66 mmol) of the este4r produced in Example 7(b) above, methyl 2-(5,6,7,8-tetrahydro-5,5,8,8-tetramethyl-2-naphthyl-6-benzo(b)furan carboxylate is obtained. (0.51 g, 85%).

Melting point: 112° C., Rf=0.55 (eluant: mixture of ethyl ether, 30% and heptane, 70%).

EXAMPLE 8

2-(5,6,7,8-tetrahydro-5,5,8,8-tetramethyl-2-naphthyl)-6-benzo(b)furan carboxylic acid In a manner analogous to Example 6, 3.00 g (8.3 mmol) of the ester produced in Example 7(c), are treated with 200 ml of 2N solution of soda in methanol. After 4 hours of heating at reflux, the solvent is evaporated. The remainder is poured into water (100 ml), acidified to pH 0 with concentrated HCl, extracted with ether (3×100 ml), dried and the solvent evaporated. The residue is recrystallized in acetontrile, yielding 2-(5,6,7,8-tetrahydro-5,5,8,8-tetramethyl-2-naphthyl)-6-benzo(b)furan carboxylic acid. (2.30 g, 80%).

Melting point: 280° C., Rf=0.75 (eluant: ethyl ether).

EXAMPLE 9

Methyl 1-t-butoxycarbonyl-2-(p-t-butyl phenyl)-6-indole carboxylate (a) methyl 3-(p-t-butylbenzamido)-4-methyl benzoate.

3.30 g (20 mmol) of methyl 3-amino-4-methyl benzoate, dissolved in 40 ml of THF, are treated at 0° C. with 3.9 g (20 mmol) of p-t-butyl benzoyl chloride, in the presence of 2.2 g (20 mmol) of triethylamine. After 2 hours, 100 ml of water are added the resulting precipitate is recovered and washed with water (3×100 ml). The recovered precipitate is dried under a vacuum and recrystallized in carbon tetrachloride.

Methyl 3-(p-t-butylbenzamido)-4-methyl benzoate is thus obtained. (5.70 g, 88%).

Melting point: 193° C., Rf=0.85 (eluant: ethyl ether).

(b) methyl 3[N(t-butoxy carbonyl)-p-t-butylbenzamido]-4-methyl benzoate.

0.97 g (3 mmol) of the ester produced in Example 9(a) is dissolved in 5 ml of THF and 1 ml of DMF. 100 mg of sodium hydride (80% in oil, 3.3 mmol) are added and the mixture is stirred for 1 hour. Thereafter 0.72 g of di-t-butyl dicarbonate is added and this mixture is stirred for 2 hours at 20° C. The mixture is then poured into water (100 ml), extracted with dichloromethane (3×50 ml). The solvent is evaporated and the remainder is then dried and recrystallized in cyclohexane. Methyl 3-(t-butoxy carbonyl-p-t-butyl benzamido)-4-methyl benzoate is obtained (1.10 g, 86%).

Melting point: 153° C., Rf=0.5 (eluant: mixture of ethyl ether, 5% and dichloromethuan, 95%).

(c) Methyl 4-bromomethyl-3-(t-butoxy carbonyl-p-t-butylbenzamido)benzoate 4.30 g (10-mmol) of the ester produced in Example 9(b) are treated with 1.80 g (10 mmol) of N-bromosuccinimide and 20 mg of benzoyl peroxide for 2 hours in carbontetrachloride at reflux. 0.20 g of N-bromosuccinimide is added and the mixture is heated at reflux for 1 hour. The solvent is evaporated and the mixture is filtered on a short silica column (5×10 cm), using, as the eluant, a mixture of chloroform, 90% and hexane, 10%. After chromotography ("Waters" Prep 500, silica column, eluant: mixture of ethyl ether, 10%-dichloromethane, 20%- and hexane, 70%), methyl 4-bromomethyl-3-(t-butoxy carbonyl-p-t-butylbenzamido)benzoate is obtained. (3.60 g, 71%).

Melting point: 135° C., Rf=0.6 (eluant: dichloromethane).

(d) Methyl 1-t-butoxyoxycarbonyl-2-(p-t-butylphenyl)-6-indolecarboxylate.

3.30 g (6.5 mmol) of the ester produced in Example 9(c), above, are dissolved in 20 ml of THF. 2.05 g (7.8 mmol) of triphenylphosphine are added and the mixture is heated at reflux for 6 hours. The mixture is then cooled to 20° C. and 1.17 ml (7.8 mmol) of DBU are added. This mixture is then heated for 30 minutes at reflux, then poured in water (100 ml) and acidified to pH 0 with a solution of concentrated HCl. The acidified reaction mixture is extracted with dichloromethane (3×100 ml). After washing with water until neutral and drying, the solvent is evaporated. The resulting residue is dissolved in dichloromethane and imperfectly purified by passage through a short silica column (5×10 cm). The solvents are evaporated and the residue recrystalized in cyclohexane, yielding methyl 1-t-butoxycarbonyl-2-(p-t-butylphenyl)-6-indolecarboxylate. (1.60 g, 61%).

Melting point: 167° C., Rf=0.7 (eluant: mixture of ethyl ether, 50% and hexane, 50%).

EXAMPLE 10

2-(p-t-butylphenyl)-6-indolecarboxylic acid 1.25 g (3.1 mmol) of the ester produced in Example 9(d) above are stirred for 2 hours with 100 ml of a 2N solution of soda in methanol, at reflux. The solvent is evaporated. The residue is taken up in water (100 ml) and extracted with ethyl ether (3×100 ml). The aqueous phase is acidified to pH 4 with a solution of 1N HCl, extracted with ether (3×100 ml), dried and the organizc phase is evaporated. The resulting residue is recrystallized acetonitrile, yielding 2-(p-t-butylphenyl)-6-indolecarboxylic acid (0.75 g, 84%).

Melting point: 297° C., Rf=0.5 (eluant: mixture of dichloromethane, 80% and methanol, 20%).

EXAMPLE 11

Methyl 1-t-butoxycarbonyl-2-(5,6,7,8-tetrahydro-5,5,8,8-tetramethyl-2-naphthyl)-6-indole carboxylate (a) Methyl 3-(5,6,7,8-tetrahydro-5,5,8,8-tetramethyl-2-naphthamido)-4-methyl benzoate.

In a manner analogous to Example 9(a), starting with 4.95 g (30 mmol) of methyl 3-amino-4-methyl benzoate and 2-(5,6,7,8-tetrahydro-5,5,8,8-tetramethyl)naphtoyl chloride (7.50 g, 30 mmol). There is obtained methyl 3-(5,6,7,8-tetrahydro-5,5,8,8-tetramethyl-2-naphthamido)-4-methyl benzoate. (9.65 g, 93%).

Melting point: 159° C., Rf=0.75 (eluant: mixture of dichloromethane, 95% and ethylether, 5%).

(b) Methyl 3-[N-t-butoxycarbonyl-(5,6,7,8-tetrahydro-5,5,8,8-tetramethyl-2-naphthamido)]-4-methyl benzoate.

In a manner analogous to Example 9(b), starting with 9.85 g (26 mmol) of the ester produced in Example 11(a), above, there is obtained methyl 3-[N-t-butoxycarbonyl-(5,6,7,8-tetrahydro-5,5,8,8-tetramethyl-2-naphthamido)]-4-methyl benzoate. (8.50 g, 67%).

Melting point: 132° C., Rf=0.8 (eluant: ethylether).

(c) Methyl 4-bromomethyl-3-[N-t-butoxycarbonyl-(5,6,7,8-tetrahydro-5,5,8,8-tetramethyl-2-naphthamido)]benzoate.

7.75 g (17.3 mmol) of the ester produced in Example 11(b), above, are treated with 3.08 g of N-bromosuccinimide and 40 g of benzoyl peroxide in 40 ml of carbon tetrachloride, at reflux, for 20 hours. The mixture is evaporated to dryness and filtered on a short column of silica (5×10 cm), by eluting with dichloromethane. The solvents are evaporated and the residue is purified by chromatography ("Waters" Prep 500, silica column, eluant: mixture of ethyl ether, 5% dichloromethane, 15%- and hexane, 80%). A mixture containing 20% of the starting product and 80% of methyl 4-bromomethyl-3-[N-(t-butoxycarbonyl-(5,6,7,8-tetramethyl-2-naphthamido)]-benzoate is obtained (7.2 g).

(d) 7.10 g of the mixture produced in Example 11(c), above, are dissolved in 40 ml of THF and treated with 3.20 g (12 mmol) of triplhenylphosphine. The mixture is heated for 4 hours at reflux and then cooled. To the cooled mixture 1.80 g (12 mmol) of DBU are added. This mixture is then stirred for 2 hours at 20° C. After treating in a manner analogous to that disclosed in Example 9(d), methyl 1-t-butoxycarbonyl-2-(5,6,7,8-tetrahydro-5,5,8,8-tetramethyl-2-naphthyl), 6-indole carboxylate is obtained (3.80 g, 56% starting with the ester produced in Example 11(b).

Melting point: 162° C., Rf=0.6 (eluant: dichloromethane).

EXAMPLE 12

2-(5,6,7,8-tetrahydro-5,5,8,8-tetramethyl-2-naphthyl)-6 indole carboyxlic acid

In a manner analogous to Example 10, starting with 3.40 (7.3 mmol) of the ester produced in Example 11(d), 2-(5,6,7,8-tetrahydro-5,5,8,8-tetramethyl-2-naphthyl)-6-indole carboxylic acid is obtained (2.30 g, 90%).

Melting point: 215° C., Rf=0.6 (eluant: a mixture of methanol, 20% and dichloromethane, 80%).

EXAMPLE 13

Methyl 2-(5,6,7,8-tetrahydro-5,5,8,8-tetramethyl-2-naphthyl)-6-indole carboxylate 1.60 g (4.6 mmol) of the acid obtained in Example 12 are dissolved in 50 ml of methanol. 0.5 ml of concentrated sulfuric acid is added and the mixture is heated at reflux for 8 hours. The methanol is evaporated and the residue is taken up in dichloromethane (200 ml) and washed with a solution of sodium bicarbonate. The organic phase is recovered and dried, and the solvent is evaporated. The resulting residue is purified by passage through a short silica column (5×10 cm) by eluting with dichloromethane, thus yielding methyl 2-(5,6,7,8-tetrahydro-5,5,8,8-tetramethyl-2-naphthyl)-6-indole carboxylate. (1.60 g, 96%).

Melting point: 202° C., Rf=0.5 (eluant: mixture of ethyl ether, 50% and heptane, 50%.).

EXAMPLE 14

Methyl 1-methyl-2-(5,6,7,8-tetrahydro-5,5,8,8-tetramethyl-2-naphthyl)-6-indole carboxylate 1.40 g (3.8 mmol) of the ester produced in Example 13, are dissolved in 20 ml of dry THF, and treated with 0.14 g (4.6 mmol) of sodium hydride (80% in oil). This mixture is stirred for 1 hour, at which point 0.65 g (4.4 mmol) of methyl iodide is added. The resulting mixture is stirred for 2 hours and then poured into water (100 ml) and extracted with dichloromethane (3×100 ml). The organic phase is dried and the solvent evaporated. The resulting residue is recrystallized in hexane, yielding methyl 1-methyl-2-(5,6,7,8-tetrahydro-5,5,8,8-tetramethyl-2-naphthyl)-6-indole carboxylate. (1.30 g, 91%)

Melting point: 156° C., Rf=0.65 (eluant: mixture of ethyl ether, 50% and hexane, 50%).

EXAMPLE 15

1-methyl-2-(5,6,7,8-tetrahydro-5,5,8,8-tetramethyl-2-naphthyl)-6-indole carboxylic acid 1.00 g (2.65 mmol) of the ester produced in Example 14, is treated in a manner analogous to that set forth in Example 12, yielding, after recrystallization in a mixture of ethyl acetate and isopropyl ether, 1-methyl-2-(5,6,7,8-tetrahydro-5,5,8,8-tetramethyl-2-naphthyl)-6-indole carboxylic acid. (0.90 g, 93%).

Melting point: 256° C., Rf=0.8 (eluant: ethyl ether).

EXAMPLE 16 methyl 2-(p-t-butylphenhyl)-5-benzimidazole carboxylate (a) methyl 4-amino-3-(p-t-butylbenzamido)benzoate 1.65 g (10 mmol) of methyl 3.4-diamino benzoate and 1.10 g (11 mmol) of triethylamine in 150 ml of ethyl ether are treated, dropwise, at 0° C. with 2.00 g (10 mmol) of p-t-butylbenzoyl chloride. The reaction mixture is then permitted to return to ambient temperature and is stirred for 1 hour. Thereafter, the reaction mixture is poured into water (100 ml), extracted with dichloromethane (3×100 ml) and dried. The solvent is evaporated and the residue is recrystallized in a mixture of isopropyl ether and cyclohexane, yielding methyl 4-amino-3-(p-t-butylbenzamido)benzoate. (2.40 g, 73%).

Melting point: 175° C., Rf=0.6 (eluant: ethyl ether).

(b) Methyl 2-(p-t-butylphenyl)-5-benzimid azole carboxylate.

2 g of the product produced in Example 16(a), above, are dissolved in 100 ml of xylene, and 20 mg of p-toluene sulfonic acid (monohydrate) is added thereto. The mixture is heated at reflux for 16 hours, by removing water in proportion to its formation. The solvent is evaporated and the residue is taken up in dichloromethane (100 ml), and then washed with a saturated solution of sodium bicarbonate. The organic phase is dried, the solvent is evaporated and the residue is purified by passage through a short column of silica (5×10 cm), by eluting with a mixture of dichloromethane, 95% and ethyl ether, 5%. The solvents are evaporated and the residue is recrystallized in a mixture of cyclohexane and isopropyl ether, yielding methyl 2-(p-t-butyl phenyl)-5-benzimidazole carboxylate. (1.40 g, 74%).

Melting point: 208° C., Rf=0.6 (eluant: ethyl ether).

EXAMPLE 17

2-(p-t-butylphenyl)-5-benzimidazole carboxylic acid 1.20 g (3.9 mmol) of the ester produced in Example 16(b) are stirred for 48 hours in 75 ml of a sodium hydroxide solution in methanol (2N). The methanol is evaporated and 100 ml of water are added to the residue. The resulting mixture is extracted and with ethyl ether, then acidified to pH 4 with a solution of 1N HCl. This mixture is extracted with ethyl ether (3×100 ml), dried and the solvent evaporated. The residue is recrystallized in a mixture of ethyl acetate and isopropyl ether, yielding 2-(p-t-butylphenyl)-5-benzimidazole carboxylic acid. (0.70 g, 61%)

Melting point: 212° C., Rf=0.6 (eluant: mixture of methanol, 20% and dichloromethane, 80%).

EXAMPLE 18 methyl 2-(5,6,7,8-tetrahydro-5,5,8,8-tetramethyl-2-naphthyl)-5-benzimidazole carboxylate (a) methyl 4-amino-3-(5,6,7,8-tetrahydro-5,5,8,8-tetramethyl-2-naphthamido)benzoate.

In a manner analogous to Example 16(a), starting with 2.70 g (16.2 mmol) and methyl 3,4-diamino benzoate and 4.05 g (16.2 mmol) of 5,6,7,8-tetrahydro-5,5,8,-tetramethyl-2-naphtoyl chloride, there is obtained, after recrystallization in a mixture of ethyl acetate and isopropyl ether, methyl 4-amino-3-(5,6,7,8-tetrahydro 5,5,8,8-tetramethyl-2-naphthamido)benzoate. (5.20 g, 84%).

Melting point: 216° C., Rf=(eluant:ethyl ether)

(b) In a manner analogous to Example 16(b), starting with 5.00 g (13 mmol) of the ester produced in Example 18(a), above, methyl 2-(5,6,7,8-tetrahydro-5,5,8,8-tetramethyl-2-naphthyl)-5-benzimidazole carboxylate is obtained (3.70 g 78%).

Melting point: 223° C., Rf=0.75 (eluant: ethyl ether)

EXAMPLE 19

2-(5,6,7,8-tetrahydro-5,5,8,8-tetramethyl-2-naphthyl)-5-benzimidazole carboxylic acid In a manner analogous to Example 17, starting with 2.90 g (8 mmol) of the ester produced in Example 18(b) treated with 150 ml of a solution of sodium hydroxide in methanol (2N), 2-(5,6,7,8-tetrahydro-5,5,8,8-tetramethyl-2-naphthyl)-5-benzimidazole carboxylic acid is obtained (2.4 g, 86%).

Melting point: 228° C., Rf=0.6 (eluant: mixture of dichloromethane, 80% and methanol, 20%).

EXAMPLE 20 methyl 2-(5,6,7,8-tetrahydro-5,5,8,8-tetramethyl-2-nphthyl)-6-benzoxazole carboxylate.

(a) methyl 3-hydroxy-4-nitro benzoate.

In a round-bottomed flask, 36.3 g (0.2 mole) of 3-hydroxy-4-nitro benzoic acid, 40 ml of methanol and 5.4 ml of concentrated sulfuric acid are introduced. The reaction mixture is heated to reflux for 8 hours. The solvent is evaporated and the remainder is taken up in water, then neutralized and finally extracted with a liter of ethyl ether. The organic phase in decanted, dried on magnesium sulfate and then the solvent is evaporated. The resulting solid is recrystallized in a hexane/cyclohexane mixture. (38.5 g, 77%).

Melting point: 89° C., Rf=0.55 (eluant: mixture of ethyl ether, 50% and hexane, 50%).

(b) methyl 4-amino-3-hydroxy benzoate.

In a round-bottomed flask 5.9 g (0.03 mole) of methyl 3-hydroxy-4-nitro benzoate, 70 ml of ethyl alcohol and 10.1 g (0.18 mole) of powdered iron are introduced. The mixture is cooled to 10° C. at which point these are added, dropwise, 10 ml of concentrated HCl. The mixture is then stirred at ambient temperature for two hours. The reaction mixture is filtered and the filtrate is evaporated. The resulting residue is taken up in a bicarbonated water/ethyl ether mixture. The organic phase is decanted and dried on magnesium sulfate. The solvent is evaporated and the resulting solid is recrystallized in a cyclohexane/isopropyl either mixture. (4.5 g, 90%).

Melting point: 121° C., Rf=0.55 (eluant: ethyl ether).

(c) In a round-bottomed flask there are introduced 3.34 g (0.02 mole) of methyl 4-amino-3-hydroxybenzoate, 4.6 g (0.02 mole) of 5,6,7,8-tetrahydro-5,5,8,8-tetramethyl-2-naphthoic acid, 1.23 g (0.2 mole) of boric acid and 200 ml of xylene. The mixture is heated at reflux for 30 hours and the water formed in separated using with a Dean-Stark separator. The reaction mixture evaporates to dryness. The residue is taken up in bicarbonated water, and then extracted with methylene chloride. The organic phase is decanted, dried on magnesium sulfate and the solvent is evaporated. The resulting product is purified by flash chromatogrphy on a silica column by eluting with methylene chloride and then crystallized in hexane (3.0 g, 41.3%).

Melting point: 149° C., Rf=0.3 (eluant: mixture of hexane, 70% and ethyl ether, 30%).

EXAMPLE 21

2-(5,6,7,8-tetrahydro-5,5,8,8-tetramethyl-2-naphthyl)-6-benzoxazole carboxylic acid In a round-bottomed flask, there are introduced 2.5 g (6.88 mmoles) of the ester produced in Example 20(c) in 200 ml of methanolic soda (2M). The reraction mixture is heated at reflux for 4 hours and evaporated to dryness, the residue is taken up in water and acidified to pH 4 with concentrated HCl. The solid which has precipitated is then filtered, dried on phosphoric anhydride and then recrystallized in an ethyl acetate tetrahydrofuran mixture. (1.5 g, 62.5%)

Melting point: 310° C., Rf=0.7 (eluant: ethyl ether).

EXAMPLE 22

Morpholide of 2-(5,6,7,8-tetrahydro-5,5,8,8-tetramethyl-2-naphthyl)-6-benzoxazole carboxylic acid (a) 2-(5,6,7,8-tetrahydro-5,5,8,8-tetramethyl-2-naphthyl)-6-benzoxazole carboxylic acid.

In a round-bottomed flask, there are introduced 6.98 g (20 mmoles) of the acid produced in Examples 21 in 100 ml of anhydrous dichloromethane. There are then added 4 ml (20 mmoles) of dicyclohexylamine and the resulting mixture is stirred for 2 hours at 20° C. The solvents are evaporated and the residue is taken up in anhydrous ether. The salt thus obtained (10.5 g) is filtered off and used as is.

This salt is introduced into a round-bottomed flask to which are added 100 ml of dry dichloromethane and 1.45 ml (20 mmols) of thionylchloride. This mixture is stirred for 4 hours at 20° C. and then evaporated to dryness to obtain a white solid (7.25 g, 99%).

(b) Morpholide of 2-(5,6,7,8-tetrahydro-5,5,8,8-tetramethyl-2-naphthyl)-6-benzoxazole carboxylic acid.

In a round-bottomed flask, there are introduced 1.05 ml (12 mmols) of morpholine and 50 ml of dichloromethane. To this mixture there are added, dropwise 1.4 g (4 mmoles) of the acid chloride produced in part (a), above, dissolved in 50 ml of dichloromethane. The mixture is stirred for 2 hours at 20° C. and poured into water. The organic phase is decanted and dried on magnesium sulfate. The solvents are evaporated and the residue is recrystallized in isopropyl ether, yielding 1.2 g of the expected product (72%).

Melting point: 149°–150° C.

EXAMPLE 23

Ethylamide of 2-(5,6,7,8-tetrahydro-5,5,8,8-tetramethyl-2-naphthyl)-6-benzoxazole carboxylic acid In a manner analogous to Example 22, starting with 12 mmoles of ethylamine and 4 mmoles of the acid chloride produced in Example 22(a), the ethylamide of 2-(5,6,7,8-tetrahydro-5,5,8,8-tetramethyl-2-naphthyl)-6-benzoxazole carboxylic acid is obtained (1.1 g, 74%).

Melting point: 164°–165° C. (recrystallized in an ethyl acetate/isopropyl ether mixture).

EXAMPLE 24

The 2-hydroxyethyl ester of 2-(5,6,7,8-tetrahydro-5,5,8,8-tetramethyl-2-naphthyl)-6-benzoxazole carboxylic acid In a round bottomed flask, there are introduced 6.4 ml (114 mmoles) of ethylene glycol, 1.9 ml (23 mmoles of pyridine and 50 ml of dichloromethane. The reaction mixture is cooled to 0° C., at which point there are added, dropwise, 1.4 g (11 mmoles) of the acid chloride produced in Example 22(a), dissolved in 50 ml of dichloromethane. This mixture is then stirred for 2 hours at 20° C. and poured into water. The organic phase is decanted and dried on magnesium sulfate. The solvents are then evaporated. The produce is rapidly chromotographed on a silica column using as the eluant a mixture of dichloromethane, 90% and ether, 10% (4.0 g, 91%).

Melting point: 126°–127° C.

EXAMPLE 25

2-(5,6,7,8-tetrahydro-5,5,8,8-tetramethyl-2-naphthyl)-6-benzoxazolyl methyl alcohol In a round-bottom flask there are introduced under a nitrogen atmosphere, 50 ml of THF, and 330 mg of LiAlH$_4$. There are then added, in small amounts, 2.0 g (5.7 mmoles) of the ester produced in Example 20(c) and the mixture is heated at reflux for 1 hour.

The mixture is then treated with a solution of the double tartrate of sodium and potassium, and filtered. The organic phase is recovered and dried on magnesium sulfate. The solvents are evaporated and the resulting residue is purified by chromatography on a silica column using as the eluant a mixture of dichloromethane, 95% and ether, 5%, The product is recrystallized in cyclohexane. (1 g, 52%).

Melting point: 125°–126° C.

EXAMPLE 26

The methyl ester of 2-[3-(1-adamantyl)-4-methoxyphenyl]-6-benzimidazole carboxylic acid (a') 2-(1-adamantyl)-4-bromoanisole.

To a suspension of sodium hydride (80% in oil, 4.32 g, 144 mmol) in 50 ml of THF, there are slowly added while maintaining the temperature at 20° C., 36.8 g (120 mmol) of 2-(1-adamantyl)-4-bromophenol obtained in Example 29 (a') and stirring for 1 hour at ambient temperature. There are then added 9 ml (144 mmol) of methyl iodide and the mixture is stirred for 2 hours at 20° C. The reaction mixture is poured into water, extracted with dry ether and evaporated. The resulting product is purified by passage over a silica column (10×30 cm) by eluting with a mixture of hexane (90%)

and dichloromethane (10%). On evaporation 26.2 g of a white solid are obtained.

Yield: 68%. Melting point: 138°–139° C.

(a) 3-(1-adamantyl)-4-methoxybenzoic acid.

In a round bottomed flask, there are introduced 5.4 g (225 m atom g) of magnesium turnings, and 30 ml of THF. To this mixture there is added, dropwise, a solution of 48.3 g (150 mmoles) of 2-adamantyl-4-bromo anisole, and 6 ml (70 mmoles) of 1,2-dibromoethane in 300 ml of THF.

This mixture is heated at reflux for 2 hours and then cooled to −70° C. A current of $CO_2$ is passed therethrough for 1 hour. The temperature of the mixture is then permitted to rise to 20° C. at which point it is poured into water, acidified to pH 1 with concentrated HCl and extracted with ethyl ether. The organic phase is decanted and dried on magnesium sulfate. The solvents are evaporated.

The resulting solid is recyrstallized in ethyl acetate (3.7 g, 86%).

Melting point: 238°–239° C.

(b) 3-(1-adamantyl)-4-methoxybenzoic acid chloride.

In a round-bottomed flask, there are introduced 200 ml of thionyl chloride to which are added, in small amounts, 35 g (122 mmoles) of the acid produced in part (a), above. The mixture is heated at reflux until the gaseous emission ceases. The mixture is then evaporated to dryness, and the residue is taken up with 100 ml of anhydrous benzene. The mixture is evaporated to dryness, yielding 3-(1-adamantyl)-4-methoxybenzoic acid chloride which is used, as is, (37 g). Melting point: 153°–154° C.

(c) Methyl ester of 4-amino-3-[3-(1-adamantyl)-4-methoxy benzamido]-benzoic acid.

In a round-bottomed flask there are introduced 3.32 g (20 mmoles) of the methyl ester of 3,4-diamino-benzoic acid, 3.1 ml (22 mmoles) of triethylamine and 100 ml of anhydrous ether. There is then added, dropwise at 0° C. a solution of the acid chloride produced in part (b) above (6.1 g, 20 mmoles), in 100 ml of ethyl ester. The temperature of the reaction mixture is raised to 20° C. and the mixture is stirred for 2 hours. Thereafter, the mixture is poured into water and the ether phase is decanted and dried on magnesium sulfate. The solvents are evaporated and the resulting solid is heated in 100 ml of isopropyl ether at reflux for 15 minutes. After the temperature of this mixture returns to 20° C. it is filtered, yielding 7.4 g of a white solid that is used, as is, in the following synthesis:

(d) Methyl ester of 2-[3-(1-adamantyl)-4-methoxyphenyl]-5-benzimidazole carboxylic acid.

In a round-bottom flask there are introduced 10.5 g (24 mmoles) of the ester product in part (c) above, 30 ml of xylene and 4.6 g (24 mmoles) of p-toluene sulfonic acid.

The mixture is heated at reflux for 12 hours by separating the water formed. It is then evaporated to dryness, and the resulting residue is taken up in a saturated solution of sodium bicarbonate.

This solution is filtered and the resulting solid purified by chromatography on a silica column using as the eluant a mixture of methylene chloride, 95% and ether, 5%. The solvents are then evaporated, yielding a white solid that is heated briefly at reflux in 400 ml of ethyl acetate. The mixture is then cooled, yielding the expected ester. (8.7 g, 87%).

Melting point: 257°–258° C.

EXAMPLE 27

Methyl ester of 2-[3-(1-adamantyl)-4-methoxy phenyl]-6-benzoxazole carboxylic acid (a) Methyl ester of 4-amino-3-[3-(1-adamantyl)-4-methoxy-benzoyloxy]-benzoic acid.

In a round-bottomed flask there are introduced 3.8 g (30 mmoles) of the methyl ester of 4-amino-3-hydroxybenzoic acid, 3.5 ml (25 mmoles) of triethylamine and 100 ml of ether. The reaction mixture is cooled to 0° C. and 7 g (23 mmoles) of the acid chloride produced in Example 26(b) dissolved in 100 ml of ethyl ether are added dropwise thereto. The mixture is then stirred at 20° C. for 4 hours and poured into water. The organic phase is decanted, dried on magnesium sulfate and the solvent evaporated. The resulting residue is recrystalized in cyclohexane, yielding 8.5 g of the product which is used, as is, for the following synthesis.

(b) Methyl ester of 2-[3-(1-adamantyl)-4-methoxyphenyl]-6-benzoxazole carboxylic acid.

In a round-bottomed flask there are introduced 8.5 g (20 mmoles) of the ester produced in part (a), above, 400 ml of xylene and 3.7 g (20 mmoles) of p-toluene sulfonic acid. This mixture is heated at reflux for 12 hours by separating the water formed and then evaporated to dryness. The residue is taken up in a saturated solution of sodium bicarbonate and then filtered. The solid obtained is purified by chromatography on a silica column using dichloromethane as the eluant.

On recrystallization in a mixture of ethyl acetate and isopropyl ether, 7.7 g (95%) of the desired ester are obtained.

Melting point: 183°–184° C.

EXAMPLE 28

2-[3-(1-adamantyl)-4-methoxyphenyl]-6-benzoxazole carboxylic acid

In a round-bottomed flask, there are introduced 6.4 g (15 mmoles) of the ester produced in Example 27(b) and a solution of soda (16 g) in 300 ml of THF and 30 ml of water.

This mixture is stirred at ambient temperature for 72 hours and the solvents are evaporated. The resulting residue is taken up in water and acidified to pH 5 with IN HCl. The resulting solid is filtered off and washed with water. The solid is then extracted with 7 liters of ethyl acetate, dried on magnesium sulfate and the solvent evaporated. The solid is then treated with 500 ml of ethyl acetate at reflux for 1 hour. After cooling and filtering, 5.9 g of the solid are obtained.

Melting point: 312°–314° C.

EXAMPLE 29

Methyl ester of 2-[3-(1-adamantyl)-4-decyloxyphenyl]-6-benzoxazole carboxylic acid (a') 2-(1-adamantyl)-4-bromophenol 34.6 g (200 mmol) of p-bromophenol and 30.4 g (200 mmol) of 1-adamantanol are dissolved in 100 ml of dichloromethane. There are slowly added 10 ml of concentrated sulfuric acid and the reaction mixture is stirred for 8 hours at ambient temperature. The reaction mixture is then poured into water, neutralized with sodium bicarbonate, extracted with methylene chloride, dried and evaporated. After recrystallization in isooctane 52.8 g of the desired product are obtained.

Yield: 86%. Melting point: 140°–141° C.

(a) 2-(1-adamantyl)-4-bromodecyloxybenzene

In a round-bottomed flask, there are introduced 3.2 g (104 mmoles) of sodium hydride (80% in oil) and 100 ml of N,N-dimethylformamide. There is then added, dropwise, a solution of 2-adamantyl-4-bromophenol (29 g, 95 mmoles) in 100 ml of N,N-dimethylformamide, and the mixture is stirred until the gaseous emission ceases. There are then added 23 ml (104 mmoles) of 1-iododecane. The mixture is stirred for 8 hours at 20° C., poured into water, dried on magnesium sulfate, and the solvents are evaporated. The products is purified by by chromatography on a silica column, (eluant: heptane).

40.7 g (96%) of 2-(1-adamantyl)-4-bromodecyloxy benzene are thus obtained. Melting point: 69°–70° C.

(b) 3-(1-adamantyl)-4-decyloxy benzoic acid.

In a manner analogous to Example 26(a) starting with 17.9 g (40 mmoles) of the derivative produced in Example 29(a), above, there is obtained, after crystallization in a mixture of ethyl acetate and ispropylether, 3-(1-adamantyl)-4-decyloxybenzoic acid (13.5 g, 82%). Melting point: 151°–152° C.

(c) 3-(1-adamantyl)-4-decyloxy benzoic acid chloride.

In a manner analogous to Example 26(b), starting with 7.45 g (18 mmoles) of 3-(1-adamantyl)-4-decyloxy benzoic acid, 7.7 g of the corresponding acid chloride are obtained (100%).

(d) Methyl esters of 4-amino-3-[3-(1-adamantyl)-4-decyloxy benzoyloxy]-benzoic acid and 4-[3-(1-adamantyl)-4-decyloxybenzamido]-3-hydroxy benzoic acid.

In a round-bottomed flask, there are introduced 3.0 g (18 mmoles) of the methyl ester of 4-amino-3-hydroxy benzoic acid, 2.8 ml (20 mmoles) of triethylamine and 100 ml of ether. The mixture is cooled to 0° C. and there is then added, dropwise, a solution of the acid chloride obtained above in part (c), in 50 ml of ether. This mixture is stirred at 20° C. for two hours and poured into water. The organic phase is decanted, dried on magnesium sulfate and the solvent is evaporated. The resulting product is purified by chromatography on a silica column by eluting with dichloromethane, yielding successively 2.2 g of the methyl ester of 4-[3-(1-adamantyl)-4-decyloxybenzamido]-3-hydroxy benzoic acid, then 5 g of the methyl ester of 4-amino-3-[3-(1-adamantyl)-4-decyloxybenzoyloxy]benzoic acid.

(e) Methyl ester of 2-[3-(1-adamantyl)-4-decyloxyphenyl]-6-benzoxazole carboxylic acid.

In a round-bottomed flask, there are introduced 6.8 g (12 mmoles) of the mixture produced in part (d) above, 300 ml of xylene, and 2.3 g (12 mmoles) of p-toluene sulfonic acid. This mixture is heated at reflux for 5 hours by separating the water which forms and then evaporated to dryness. The resulting residue is taken up in a saturated solution of sodium bicarbonate, and extracted with dichloromethane. The organic phase is decanted, dried on magnesium sulfate and the solvent evaporated. The resulting residue is recrystallized in a mixture of ethylacetate and isopropyl ether, yielding 5.3 g (81%) of the methyl ester of 2-[3-(1-adamantyl)-4-decyloxyphenyl]-6-benzoxazole carboxylic acid.

Melting point: 127°–128° C.

EXAMPLE 30

2-[3-(1-adamantyl)-4-decyloxyphenyl]-6-benzoxazole carboxylic acid

In a manner analogous to Example 28, starting with 4.6 g (8.5 mmoles) of the ester produced in Example 29(e), there are obtained 3.9 g (88%) of 2-[3-(1-adamantyl)-4-decyloxyphenyl]-6-benzoxazole carboxylic acid.

Melting point: 200°–201° C. (recrystallized in ethyl acetate).

EXAMPLE 31

Methyl ester of 2-[3-(1-adamantyl)-4-methoxy phenyl]-6-benzo(b)furane carboxylic acid (a) Methyl ester of 3-[3-(1-adamantyl)-4-methoxybenzoyloxy]-4-methyl benzoic acid In a manner analogous to Example 5(a), starting with 4.99 g (30 mmoles) of the ester of 3-hydroxy-4-methyl benzoic acid and 9.14 g (30 mmoles) of the acid chloride produced in Example 26(b), there are obtained, after chromotography on a silica column (eluant: a mixture of dichloromethane, 50% and hexane, 50%), 12 g of the desired ester (92%). Melting point: 110° C.

(b) Methyl ester of 3-[3-(1-adamantyl)-4-methoxy benzoyloxy]-4-bromoethyl benzoic acid.

In a manner analogous to Example 5(b), starting with 1.70 g (3.9 moles) of the ester produced in part (a) above, 0.70 g of N-bromosuccinimide and 20 mg of benzoyl peroxide in 15 ml of carbon tetrachloride brought to reflux under a nitrogen atmosphere for 3 hours, there is obtained, after chromotagraphy on a silica column (eluant: mixture of ethyl ether, 30% and hexane, 70%), a mixture of the desired product and the starting product. This mixture is used, as is, in the following synthesis.

(c) Methyl ester of 2-[3-(1-adamantyl)-4-methoxy phenyl]-6-benzo(b)furane carboxylic acid.

The mixture obtained in part (b), above is dissolved in 100 ml of dry THF. There are then added 4.17 g (16 mmoles) of triphenyl phosphine and this mixture is heated for 4 hours at reflux.

It is then cooled to ambient temperature and 2.4 ml (16 mmoles) of diazabicycloundecene (DBU) are added dropwise. The mixture is stirred for 40 minutes at 35° C. At the end of the addition the mixture is poured into water, acidified to pH 1 (with 6N HCl) and extracted with ether.

The organic phase is washed with water, dried on magnesium sulfate and the solvent evaporated.

The resulting residue is chromatographed on a silica column (eluant: a mixture of ethyl ether, 20% and hexane, 80%). The fluorescent fractions (under UV irradiation at 254 nm) are recovered and solvents evaporated, yielding 1.82 g (27% yield for steps 31(b) and 31(c) combined) of the desired ester. Melting point: 180° C.

EXAMPLE 32

2-[2-(1-adamantyl)-4-methoxyphenyl]-6benzo(b)furane carboxylic acid

In a manner analogous to Example 8, starting with 1.52 g (3.65 mmoles) of the ester produced in Example 31(c), there is obtained 2-[3-(1-adamantyl)-4-methoxyphenyl]-6-benzo(b) furan carboxylic acid. (1.32 g, 90%). Melting point: 290° C.

EXAMPLE 33

Methyl ester of 2-[3-(1-adamantyl)-4-methoxyphenyl]-6-benzo(b)thiophene carboxylic acid (a) Methyl ester of 4-[3-(1-adamantyl)-4-methoxybenzoylthio]-4-methyl benzoic acid In a manner analogous to Example 1(a), starting with 5.47 g (30 mmoles) of methyl 3-mercapto-4-methyl benzoate, 4.6 ml (33 mmoles) of triethylamine, and 9.14 g (30 mmoles) of the acid chloride produced in Example 26(b), the methyl ester of 4-[3-(1-adamantyl)-4-methoxybenzoylthio]-4-methyl benzoic acid is obtained (12.83 g, 95%). Melting point: 140° C.

(b) Methyl ester of 4-[3-(1-adamantyl)-4-methoxybenzoylthio]-4-bromomethyl benzoic acid.

In a manner analogous to Example 1(b), starting with 12.50 g (28 mmoles) of the ester obtained in part (a), above, 4.94 g (28 mmoles) of N-bromosuccinimide and 100 mg of benzoyl peroxide, in 200 ml of carbon tetrachloride, there is obtained, after chromatography on a silica column (eluant: a mixture of ethyl ether, 40% and hexane, 60%), a mixture containing the starting product and the desired product which is used, as is, for the following synthesis.

(c) Methyl ester of 2-[3-(1-adamantyl)-4-methoxy phenyl]-6-benzo(b)thiophene carboxylic acid.

In a manner analogous to Example 1(c), starting with all of the mixture produced above in part (b), 4.55 g (17.5 mmoles) of triphenylphosphine and 2.60 ml (17.5 mmoles) of DBU, there is obtained, after chromatography on a silica column (eluent: a mixture of dichloromethane, 40% and hexane, 60%) the desired ester. (1.68 g–14% yield for steps 33(b) and 33(c) combined. Melting point: 172° C.

EXAMPLE 34

2-[3-(1-adamantyl)-4-methoxyphenyl]-6-benzo(b)thiophene carboxylic acid

In a manner analogous to Example 2, starting with 1.32 g of the ester produced in Example 33(c), 1.15 g (90%) of the corresponding acid are obtained. Melting point: 305° C.

EXAMPLE 35

Methyl ester of 2-(3-t-butyl-4-methoxy phenyl)-6-benzo (b) furan carboxylic acid (a) 3-t-butyl-4-methoxy benzoic acid.

In a manner analogous to Example 26(a), starting with 12.16 g (50 mmoles) of 4-bromo-3-t-butyl-methoxybenzene, 1.34 g (55 mn atom g) of magnesium, an excess of $CO_2$ gas, 8.31 g (80%) of 3-t-butyl-4-methoxy benzoic acid having a melting point of 190° C. are obtained.

(b) 3-t-butyl-4-methoxybenzoic acid chloride.

In a manner analogous to Example 22(a), starting with 19.0 g (92 mmoles) of the acid obtained in part (a), above, 18.3 ml (92 mmoles) of dicyclohexylamine, the salt obtained being treated with 6.7 ml (92 mmoles) of thionyl chloride, 19.8 g (95%) of the acid chloride (pale yellow oil) are obtained which is employed, as is, in the following synthesis.

(c) Methyl ester of 3-[3-t-butyl-4-methoxy-benzoyloxy]-4-methyl benzoic acid.

In a manner analogous to Example 5(a), starting with 14.5 g (87 mmoles) of methyl 3-hydroxy-4-methyl benzoate and 19.8 g (87 mmoles) of the acid chloride produced in part (b), above, there is obtained, after chromotography on a silica column (eluant: a mixture of dichloromethane, 60% and hexane, 40%) the methyl ester of 3-[3-t-butyl-4-methoxybenzoyloxy]-4-methyl benzoic acid. (27.7 g, 94%) Melting point: 152° C.

(d) Methyl ester of 4-bromomethyl-3-(3-t-butyl-4-methoxybenzoyloxy)-benzoic acid.

In a manner analogous to Example 31(b), starting with 27.3 g (76.5 mmoles) of the ester produced in part (c) above, and 13.6 g (76.5 mmoles) of N-bromosuccinimide, by using 100 mg of benzoyl peroxide as a catalyst, there is obtained, after chromatography on a silica column (eluant: a mixture of dichloromethane, 60% and hexane, 40%), a mixture of the starting product and the monobrominated product, containing traces of the dibrominated product. This mixture is used, as is, for the following synthesis.

(e) Methyl ester of 2-(3-t-butyl-4-methoxyphenyl)-6-benzo(b)furan carboxylic acid.

The mixture obtained above in part (d), 27.6 g, is dissolved in 100 ml of dry THF. There are then added 16.6 g (63 mmoles) of triphenylphosphine, and the mixture is heated at reflux for 4 hours.

The mixture is then cooled to 20° C. at which point 9.5 ml (63 mmoles) of DBU are added dropwise, under a nitrogen atmosphere. At the end of the addition the mixture is stirred again for 20 minutes at 80° C., poured into water, acidified pH 1 (with 6N HCl) and extracted three times with 200 ml of dichloromethane.

The organic phase is washed with a saturated solution of sodium chloride, dried on magnesium sulfate and the solvents are evaporated. The resulting residue is purified by chromatography on a silica column (eluant: a mixture of dichloromethane, 40% and hexane, 60%).

The fluorescent fractions (under UV irradiation at 254 nm) are recovered and the solvents are evaporated, yielding, the methyl ester of 2-(3-t-butyl-4-methoxyphenyl)-6-benzo (b) furan carboxylic acid. (11.2 g, 43%). Melting point: 179° C.

EXAMPLE 36

2-(3-t-butyl-4-methoxyphenyl)-6-benzo(b)furan carboxylic acid

In a manner analogous to Example 8, starting with 7.64 g (22.5 mmoles) of the ester produced in Example 35(e) treated with a mixture of methanol (500 ml) and aqueous soda (135 ml, 5N), there is obtained 2-(3-t-butyl-4-methoxyphenyl)-6-benzo(b)furan carboxylic acid. (6.74 g, 92%) Melting point: 235° C.

EXAMPLE 37

Methyl ester of 2-[3-(1,1-dimethyldecyl)-4-methoxyphenyl]-6-benzo (b) furan carboxylic acid (a) 4-bromo-2-(1,1-dimethyldecyl)-phenol.

A mixture of 2-methyl-1-undecene (35.6 g, 211 mmoles), parabromphenol (36.6 g, 211 mmoles) and Dowex 50×12 resin (100–200 mesh) previously washed with water, rinsed with acetone and oven dried for 3 hours at 80° C., is heated at 100°–110° C. for 48 hours. The mixture is then cooled to ambient temperature and chromatographed on a silica column (eluant: a mixture of dichloromethane, 40% and hexane, 60%), yielding 4-bromo-2-(1,1-dimethyldecyl)-phenol in the form of a pale yellow oil. (30.85 g, 43%).

The product is used, as is, for the following synthesis.

(b) 4-bromo-2-(1,1-dimethyldecyl)anisole.

The compound obtained above in part (a), (30.85 g, 90 mmoles), is dissolved in 100 ml of dry THF and then treated with 2.7 g (90 mmoles) of sodium hydride (80% in oil ) which is added in small fractions. At the end of the addition, the mixture is stirred for 30 minutes at ambient temperature. 12.8 g (90 mmole) of methyl iodide are then added and this mixture is stirred for 2 hours at 20° C. The solvent is evaporated and the residue is purified by chromatography on a silica column (eluant: a mixture of dichloromethane, 40% and hexane, 60%).

After evaporation of the solvents, the desired product in the form of a yellow oil is obtained. (29.3 g, 91%).

(c) 3-(1,1-dimethyldecyl)-4-methoxy benzoic acid.

The brominated derivative obtained in part (b) above (28.46 g, 80 mmoles), dissolved in 80 ml of dry THF, is slowly added to magnesium turnings (2.34 g, 96 mAt g) and a crystal of iodine. At the start of the addition, the mixture is heated until the reaction is initiated (establishment of a reflux). This reflux if then maintained by the rate of addition of the brominated derivative.

At the end of the addition, the mixture is stirred for 30 minutes at 50° C., cooled to 0° C. and a current of $CO_2$ gas is passed therethrough for 3 hours.

The THF is then evaporated and 300 ml of water are added. The mixture is acidified to pH 1 (by using 6N HCl) and extracted three times with 30 ml of ethyl ether. The organic phase is washed with a saturated solution of NaCl, dried on magnesium sulfate and the solvents are evaporated.

The resulting solid is washed with 50 ml of cold hexane, and oven dried at 80° C., yielding 15.25 g of 3-(1,1-dimethyldecyl)-4-methoxy benzoic acid (59%). Melting point: 112° C.

(d) 3-(1,1-dimethyldecyl)-4-methoxy benzoic acid chloride.

In a manner analogous to Example 22(a), starting with 14.4 g (44.8 mmoles) of the acid obtained in part (c) above, 9 ml (44.8 mmoles) of dicyclohexylamine, the salt obtained being treated with 3.26 ml (44.8 mmoles) of thionyl chloride for 16 hours at 20° C., the crude acid chloride is obtained and is employed, as is, for the following steps.

(e) Methyl ester of 3-[3-(1,1-dimethyldecyl)-4-methoxybenzoyloxy]-4-methyl benzoic acid.

In a manner analogous to Example 35(c), starting with 6.98 g (42 mmoles) of methyl 3-hydroxy-4-methyl benzoate, all of the crude acid chloride produced in Example 27(d) and 4.25 g (42 mmoles) of triethylamine, there is obtained the methyl ester of 3-[3-(1,1-dimethyldecyl)-4-methoxybenzoyloxy]-4-methyl benzoic acid (17.84 g, 91% yield for steps 37(d) and 37(e) combined), under the form of a yellow oil which crystallizes. Melting point: 90° C.

(f) Methyl ester of 4-bromomethyl-[3-(1,1-dimethyldecyl)-4-methoxybenzoyloxy]-benzoic acid.

In a manner analogous to Example 35(d), starting with the 17.4 g (37 mmoles) of the ester produced above in part (e), and 6.60 g (37 mmoles) of N-bromosuccinimide, there is obtained, after purification by chromatography on a silica column (eluant: a mixture of ethyl ether, 40% and hexane, 60%), a mixture containing the desired monobrominated product, the starting product, and traces of the dibrominated derivative. This mixture is used, as is, for the following step:

(g) Methyl ester of 2-[3-(1,1-dimethyldecyl)-4-methoxyphenyl]-6-benzo(b)-furan carboxylic acid.

In a manner analogous to Example 35(e), starting with all of the mixture obtained in part (f) above, 9.73 g (37 mmoles) of triphenylphosphine and 5.5 ml (37 mmoles) of DBU, there are obtained, after three recrystallizations in hexane, 3.02 g of the methyl ester of 2-[3-(1,1-dimethyldecyl)-4-methoxy phenyl]-6-benzo(b)furan carboxylic acid for a yield of 18% for the combination of steps 37(f) and 37(g). Melting point: 95° C.

EXAMPLE 38

2-[3-(1,1-dimethyldecyl)-4-methoxyphenyl]-6-benzo(b)furan carboxylic acid

In a manner analogous to Example 36, starting with 1.85 g (4 mmoles) of the ester produced in Example 37(g), 2-[3-(1,1-dimethyldecyl)-4-methoxyphenyl]-6-benzo(b)furan carboxylic acid is obtained [1.47 g, 82%]. Melting point: 150° C.

EXAMPLE 39

2-[3-(1-adamantyl)-4-methoxyphenyl]-5-benzimidazole carboxylic acid

In a round-bottomed flask, there are introduced 7.8 g (19 mmoles) of the ester produced in Example 26(d) and 300 ml of 2N methanolic soda. The mixture is heated at reflux for 24 hours and evaporated to dryness. The reside is taken up in water and acidified to pH 5 with HCl. The resulting solid is filtered off, and washed with water. The solid is then dried under a vacuum in the presence of $P_2O_5$. The solid is extracted with THF (1 liter). Then the THF is evaporated after filtering the insolubles. The product is heated at reflux for 1 hour in a mixture of THF (300 ml) and ethyl acetate (300 ml). After cooling, the solid is filtered, yielding 7 g (93%) of 2-[3-(1-adamantyl)-4-methoxyphenyl]-5-benzimidazole carboxylic acid. Melting point: 358°–359° C.

EXAMPLE 40

Methyl ester of 2-[3-(1-adamantyl-4-hydroxyphenyl]-5-benzimidazole carboxylic acid.

(a) 2-(1-adamantyl)-4-bromo-t-butyl dimethyl siloxybenzene.

In a round-bottomed flask, there are introduced 30.7 g (100 mmoles) of 2-(1-adamantyl)-4-bromophenol, 15.4 ml (110 mmoles) of triethylamine, 500 mg (4 mmoles) of 4(N,N-dimethylamino)pyridine and 200 ml of THF.

Under a nitrogen atmosphere, a solution of 15.7 g (104 mmoles) of t-butyldimethylsilyl chloride in 100 ml of DMF is added dropwise. The resulting mixture is stirred for 4 hours, poured into water and extracted with ether. The organic phase is decanted. After washing with water and drying on magnesium sulfate, the solvents are evaporated. The resulting residue is purified by passage through a silica column by eluting the hexane, yielding 3.62 g of the expected product. Melting point: 111°–112° C.

(b) 3-(1-adamantyl)-4-t-butyldimethylsilyloxybenzoic acid.

In a round-bottomed falsk, there are introduced 1.18 g (48.8 m Atg) of magnesium and 50 ml of THF. 13.7 g (32.5 mmoles) of the product produced in part (a), above, in 100 ml of THF are added, dropwise, and the mixture is heated at reflux for hours. The mixture is then cooled to −78° C. and a current of $CO_2$ gas is passed through the reaction mixture. Thereafter the temperature of the reaction mixture is permitted to return to ambient temperature at which point it is poured into water and acidified to pH 1 with 5N HCl. After extraction with ether and known treatment, the resulting solid is heated in 200 ml of isopropyl ether at reflux.

After cooling, the solid is filtered, yielding 8.2 g (65%) of 3-(1-adamantyl)-4-t-butyldimentylsilyloxy benzoic acid. Melting point: 245°–246° C.

(c) 3-(1-adamantyl)-4-t-butyldimethylsilyloxy benzoic acid chloride.

In a round-bottomed flask, there are introduced 6.45 g (16.7 mmoles) of the acid produced in part (b), above, 3.3 ml (16.7 mmoles) of dicyclohexylamine and 100 ml of methylene chloride. The mixture is stirred at ambient temperature for 2 hours and 1.35 ml (18.4 mmoles) of thionyl chloride are added. This mixture is stirred for 2 hours and then evaporated to dryness. The residue is taken up in 200 ml of ether. The dicyclohexylammonium chloride is filtered off and the solvents are evaporated, yielding 6.9 g of a solid which is used, as is, for the following step.

(d) Methyl ester of 4-amino-3-[3-(1-adamantyl)-4-t-butyl dimethylsilyloxy benzamido]benzoic acid.

In a round-bottomed flask, there are introduced 2.77 g (16.7 mmoles) of methyl 3,4-diamino benzoate, 2.6 ml (18.4 mmoles) of triethlamine and 100 ml of ether. A solution of 6.75 g (16.7 mmoles) of the acid chloride produced in part (c), above, in 100 ml of ether is added dropwise and the mixture is stirred for 2 hours at 20° C. It is then poured into water and extracted with methyl chloride. The organic phase is decanted, dried on magnesium sulfate and the solvents are evaporated. The resulting residue is purified by passage on a silica column by eluting with a mixture of dichloromethane, 95% and ether, 5%, yielding 6.9 g (78%) of the expected ester. Melting point: 216°-217° C.

(e) Methyl ester of 2-[3-(1-adamantyl)-4-t-butyl dimethysilyloxy phenyl]-5-benzimidazole carboxylic acid.

In a round-bottomed flask, there are introduced 6.3 g (11.6 mmoles) of the product produced in part (d), above, 2.2 g (11.6 mmoles) at p-toluene sulfonic acid and 100 ml of xylene. The mixture is heated at reflux for 2 hours and evaporated to dryness. The residue is taken up in a saturated sodium bicarbonate solution and extracted with methylene chloride. The organic phase is decanted, dried on magnesium sulfate and the solvent is evaporated. The residue is purified by passage through a silica column (eluant: a mixture of dichloromethane, 95% and ether, 5%), yielding 5.5 g (92%) of the expected ester. Melting point: 277°-278° C.

(f) Methyl ester of 2-[3-(1-adamantyl)-4-hydroxy]-5-benzimidazole carboxylic acid.

In a round-bottomed flask, there are introduced 5.2 g (10 mmoles) of the ester produced in part (e) above and 100 ml of THF. 11 ml (11 mmoles) of a solution of tetrabutylammonium fluoride in THF, are added dropwise. The mixture is stirred for 2 hours and poured into water. The solid is filtered off, washed with water and extracted with THF. The THF is evaporated and a while solid is recovered and heated in a mixture of 600 ml of ethyl acetate and 100 ml of THF. After the temperature of the mixture returns to ambient temperature, the resulting solid is filtered. (3.8 g; 95%). Melting point: 328°-330° C.

EXAMPLE 41

Methyl ester of 2-(5,6,7,8-tetrahydro-5,5,8,8-tetramethyl-2-naphthyl)-6-benthiazole carboxylic acid (a) Methyl ester of 4-aminto-3-(5,6,7,8-tetrahydro-5,5,8,8-tetramethyl-2-naphtolythio) benzoic acid.

In a round-bottomed flask, there are introduced 5.4 g (14.8 mmoles) of methyl 4,4-diamino-3,3'-dithiodibenzoate, 3.9 g (14.8 mmoles) of triphenyl phosphine, 75 ml of dioxane and 5 ml of water. The mixture is heated at reflux under a nitrogen atmosphere for 4 hours and then cooled to 20° C. 6.2 ml (44.5 mmoles) of triethylamine are added dropwise and then 7.4 g (29.6 mmoles) of 5,6,7,8-tetrahydro-5,5,8,8-tetramethyl-2-naphthoic acid chloride dissolved in 50 ml of ether are added. The mixture is stirred for 1 hour at 20° C., poured into water and extracted with ether. The organic phase is decanted, dried on magnesium sulfate and the solvent evaporated. The residue is recrystallized in a mixture of isopropyl ether, 66% and ethyl acetate 33%, yielding 8 g of the expected ester (68%). Melting point: 154°-155° C.

(b) Methyl ester of 2-(5,6,7,8-tetrahydro-5,5,8,8-tetramethyl-2-naphthyl)-6-benzothiazole carboxylic acid In a round-bottomed flask, there are introduced 9 g (22.6 mmoles) of the ester produced in part (a), above, 4.3 g (22.6 mmoles) of p-toluenesulfonic acid and 200 ml of xylene.

The mixture is heated at reflux for 2 hours and evaporated to dryness. The residue is taken up in dichloromethane and washed with a saturated solution of sodium bicarbonate. After conventional treatment, a residue is obtained which is recrystallized in isopropyl ether, yielding 8.2 g (95%) of the methyl ester of 2-(5,6,7,8-tetrahydro-5,5,8,8-tetramethyl-2-naphthyl)-6-benzothiazole carboxylic acid. Melting point: 143°-144° C.

EXAMPLE 42

2-(5,6,7,8-tetrahydro-5,5,8,8-tetramethyl-2-naphthyl)-6-benzothiazole carboxylic acid In a round-bottomed flask, there are introduced 5.6 g (14.7 mmoles) of the ester produced in Example 41(b), 200 ml of a 2N solution of soda in methanol and 100 ml of THF. The mixture is stirred for 4 hours at 20° C. and evaporated to dryness. The residue is taken up in water and acidified to pH 5 with 1N HCl. The resulting solid is filtered off and washed with water until neutral. The solid is extracted with ether, dried on magnesium sulfate and the solvent is evaporated. The residue is then recrystallized in ethyl acetate, yielding 4 g (75%) of 2-(5,6,7,8-tetrahydro-5,5,8,8-tetramethyl-2-naphthyl)-6-benzothiazole carboxylic acid. Melting point: 292°-293° C.

EXAMPLE 43

Methyl ester of 2-(4,4-dimethyl-2,3-dihydro-1-benzopyran-6-yl)-5-benzimidazole carboxylic acid (a) 4,4-dimethyl-2,3-dihydro-1-benzopyran-6-carboxylic acid.

To a solution of soda (21 g) in 110 ml of water cooled to −5° C., there are added, 9 ml of bromine. After 15 minutes, 6 g of 6 acetyl-4,4-dimethyl-2,3-dihydro-1-benzopyran in dioxane (50 ml) are added.

The temperature of the mixture is permitted to return to 20° C. and it is then heated to 50° C. After re-cooling, 70 ml of a solution of 9.2 g of sodium metabisulfite are added and then 42 ml of concentrated HCl are added. The mixture is diluted with water and filtered. The precipitate is washed until neutral. After crystallization in a mixture of acetone-water, the expected acid with a 90% yield is obtained.

(b) 4,4-dimethyl-2,2-dihydro-1-benzopyran-6-carboxylic acid chloride.

In a round-bottomed flask, 90 mg (0.43 mmole) of the acid obtained in part (a) above are suspended in 0.8 ml of dry dichloromethane.

There are then added, 87 μm (0.43 mmole) of dicyclohexylamine and the reaction mixture becomes clear. The mixture is then stirred for 30 minutes at ambient temperature and 32 μl (0.43 mmole) of thionyl chloride are added.

After stirring overnight at ambient temperature, the dicylohexylamine hydrochloride is filtered and the dichloromethane is evaporated, yielding a product which is used, as is, in the following step.

(c) Methyl ester of 4-amino-3-(4,4-dimethyl-2,3-dihydro-1-benzopyran-6-carboxamido)benzoic acid.

The crude product obtained in part (b) above is dissolved in 2 ml of ethyl ether and a mixture of 72.5 mg (0.43 mmole) of the methyl ester of 3,4-diamino benzoic acid, 61 μl (0.43 mmole) of triethylamine and 2 ml of ether is added dropwise.

The mixture is stirred for 2 hours at ambient temperature, then poured into water (20 ml) and extracted with 3 fractions of 10 ml of ethyl ether. The organic phase is washed with a saturated solution of sodium hydride, dried on magnesium sulfate and filtered. The solvent is evaporated, and the resulting residue is chromatographed on a silica column (eluant: a mixture of ether, 80% and hexane, 20%), yielding 82 mg (53%) of the expected product. Melting point: 213° C.

(d) Methyl ester of 2-(4,4-dimethyl-2,3-dihydro-1-benzopyran-6-yl)-5-benzimidazole carboxylic acid.

In a round-bottomed flask there are introduced the ester produced in part (e), above, (82 mg; 0.23 mmole), 44 mg (0.23 mmole) of p-toluenesulfonic acid monohydrate and 5 ml of xylene. The mixture is heated at reflux for 1 hour, cooled to 20° C. and chromatographed on a silica column (eluant: a mixture of ether, 80% and hexane, 20%) yielding 20 mg (26%) of the methyl ester of 2-(4,4-dimethyl-2,3-dihydro-1-benzopyran-6-yl)-5-benzimidazole carboxylic acid. Melting point: 110°–115° C.

EXAMPLES OF COMPOSITIONS

A—Examples of Orally Administered Compositions

EXAMPLE 1'

0.2 g Tablet
Compound of Example 4—0.001 g
Starch—0.114 g
Dicalcium phosphate—0.020 g
Silica—0.020 g
Lactose—0.030 g
Talc—0.010 g
Magnesium Stearate—0.005 g In this Example, the compound of Example 4 can be replaced by the same amount of the compound of Example 34.

EXAMPLE 2'

0.5 g Tablet, formula of the powder:
Compound of Example 1—0.001 g
Cornstarch—0.150 g
Magnesium stearate—0.250 g
Sucrose, sufficient amount for—0.500 g
The powder is packaged in a gelule composed of gelatin and titanium dioxide. In this Example, the compound of Example 1 can be replaced by the same amount of the compound of Example 35.

EXAMPLE 3'

0.4 g capsulse containing the following suspension
Compound of Example 8—0.005 g
Glycerin—0.200 g
Sucrose—0.050 g
Polyethylene glycol 400—0.050 g
Purified water, sufficient amount for—0.400 g.

This suspension is packaged in a capsule composed of gelatin, glycerine, titanium dioxide and water. In this Example, the compound of Example 8 can be replaced by the same amount of the compound of Example 31.

EXAMPLE 4'

Drinkable suspension in 5 ml ampoules.
Compound of Example 19—0.001 g
Glycerine—0.500 g
Sorbitol, 70%—0.500 g
Sodium sacharin—0.010 g
Methyl parahydroxy benzoate—0.040 g
Flavor, sufficient amount
Purified water, sufficient amount for 5.000 ml.

In this Example, the compound of Example 19 can be replaced by the same amount of the compound of Example 39.

B. Examples of Topically Applied Compositions

EXAMPLE 5'

Ointment
Compound of Example 4—0.001 g
Stearyl alcohol—3.000 g
Lanolin—5.000 g
Petrolatum—15.000 g
Distilled water, sufficient amount for—100.000 g

EXAMPLE 6'

Non-ionic oil-in-water cream
Compound of Example 2—0.050 g
Cetyl alcohol—3.000 g
Stearyl alcohol—3.400 g
Cetyl alcohol oxyethylenated with 20 moles of ethylene oxide—0.630 g
Stearyl alcohol oxyethylenated with 20 moles of ethylene oxide—1.470 g
Glycerol monostearate—2.000 g
Petrolatum oil—15.000 g
Glycerine—10.000 g
Preservatives, sufficient amount
Distilled water, sufficient amount for—100.000 g In this Example, the compound of Example 2 can be replaced by the same amount of the compound of Example 34.

EXAMPLE 7'

Ointment
Compound of Example 1—0.020 g
Isopropylmyristate—81.700 g
Liquid petrolatum oil—9.100 g
Silica, sold by Degussa under the trade name "Aerosil 200"—9.180 g In this Example, the compound of Example 1 can be replaced by the same amount of the compound of Example 35.

EXAMPLE 8'

Anionic oil-in-water cream
Compound of Example 14—0.010 g
Sodium dodecyl sulfate—0.800 g Glycerol—2.000 g
Stearyl alcohol—20.000 g
Triglycerides of capric/caprylic acids, sold by Dynamit Nobel under the trade name name "Miglyol 812"—20.000 g
Preservative, sufficient amount
Demineralized water, sufficient amount for—100.000 g

EXAMPLE 9'

Gel
Compound of Example 19—0.005 g
Hydroxypropyl cellulose, sold by Hercules under the trade name "Klucel HF"—2.000 g
Water/ethanol (50:50) sufficient amount for—100.000 g In this Example, the compound of Example 19 can be replaced by the same amount of the compound of Example 39.

EXAMPLE 10'

Collyrium
Compound of Example 19*—0.005 g
Na₂HPO₄—0.1M—80.000 ml
Na₂H₂PO₄—0.1M—20.000 ml
*100% of the particles of this compound must have a diameter less than 25 microns.

This collyrium is a suspension having a pH of 7 (pH of the lacrymal fluid) and isotonic relativel to tears. After packaging in an appropriate ampoule, the product is sterilized. The product must be vigorously shaken before use.

What is claimed is:

1. An aromatic heterocyclic compound having the formula

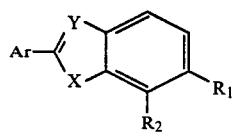

wherein
$R_1$ represents

$R_3$ represents —$OR_4$ wherein $R_4$ represents hydrogen, alkyl having 1-20 carbon atoms, mono or polyhydroxy alkyl,
$R_2$ represents hydrogen or —$CH_3$,
Ar represents an aromatic radical having the following formula

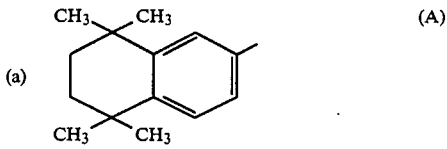

Y represents CH and
X represents sulfur.

2. The compound of claim 1 wherein said monohydroxyalkyl has 2-3 carbon atoms and is selected from the group consisting of 2-hydroxyethyl and 2-hydroxypropyl and wherein said polyhydroxy alkyl is derived from glycerol, pentaerythritol or mannitol.

3. The compound of claim 1 having the formula

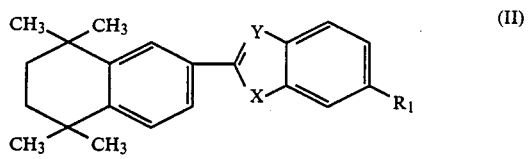

wherein
$R_1$ represents

$R_3$ represents —$OR_4$,
$R_4$ represents hydrogen, —$CH_3$ or —$CH_2CH_2OH$,
Y represents CH and
X represents sulfur.

4. The compound of claim 1 selected from
methyl 2-(5,6,7,8-tetrahydro-5,5-8,8-tetramethyl-2-naphthyl)-6-benzo(b)thiophene carboxylate,
2-(5,6,7,8-tetrahydro-5,5,8,8,-tetramethyl-2-naphthyl)-6-benzo(b)thiophene carboxylic acid.

5. A pharmaceutical composition for enteral, parenteral, topical or ocular administration comprising in a pharmaceutically acceptable carrier an effective amount of the compound of claim 1.

6. The composition of claim 5 for topical application wherein said compound is present in an amount ranging from 0.0005 to about 5 percent by weight, based on the total weight of said composition.

* * * * *